US012558062B2

(12) United States Patent
Robert et al.

(10) Patent No.: US 12,558,062 B2
(45) Date of Patent: Feb. 24, 2026

(54) RETROSPECTIVE TRANSMIT FOCUSING USING A TRANSMIT SPEED SYSTEMS, DEVICES, AND METHODS

(71) Applicant: KONINKLIJKE PHILIPS N.V., Eindhoven (NL)

(72) Inventors: Jean-Luc Francois-Marie Robert, Cambridge, MA (US); Changhong Hu, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 327 days.

(21) Appl. No.: 18/038,885

(22) PCT Filed: Nov. 23, 2021

(86) PCT No.: PCT/EP2021/082576
§ 371 (c)(1),
(2) Date: May 25, 2023

(87) PCT Pub. No.: WO2022/117393
PCT Pub. Date: Jun. 9, 2022

(65) Prior Publication Data
US 2023/0408662 A1     Dec. 21, 2023

Related U.S. Application Data

(60) Provisional application No. 63/119,831, filed on Dec. 1, 2020.

(51) Int. Cl.
*A61B 8/00*     (2006.01)
*G01S 7/52*     (2006.01)
(52) U.S. Cl.
CPC ........... *A61B 8/44* (2013.01); *G01S 7/52036* (2013.01); *G01S 7/52049* (2013.01); *G01S 7/52095* (2013.01)

(58) Field of Classification Search
CPC ... A61B 8/44; G01S 7/52036; G01S 7/52049; G01S 7/52095
See application file for complete search history.

(56) References Cited

U.S. PATENT DOCUMENTS 8,137,272 B2     3/2012   Cooley et al.
2009/0306512 A1   12/2009   Loftman et al.
(Continued)

FOREIGN PATENT DOCUMENTS

WO     2013148673 A1   10/2013
WO     2019219485 A1   11/2019
WO     2019219549 A1   11/2019

OTHER PUBLICATIONS

International Search Report and Written Opinion for PCT/EP2021/082576; Mailing date: Feb. 24, 2022, 11 pages.

*Primary Examiner* — Dixomara Vargas

(57) ABSTRACT

An ultrasound imaging system includes an array of acoustic elements configured to transmit ultrasound energy at a first transmit speed and receive echoes associated with the ultrasound energy transmitted at the first transmit speed. The system further includes a processor circuit in communication with the array of acoustic elements. The processor is configured to generate a plurality of multilines based on the received echoes, determine a second transmit speed, determine a set of transmit focus delays based on the second transmit speed, adjust the plurality of multilines using the set of transmit focus delays, generate an image based on the adjusted plurality of multilines, and output the generated image to a display in communication with the processor circuit.

15 Claims, 9 Drawing Sheets

(56)     References Cited

U.S. PATENT DOCUMENTS

| | | | | |
|---|---|---|---|---|
| 2010/0076312 A1* | 3/2010 | Katsuyama | ............... | A61B 8/00 |
| | | | | 600/443 |
| 2012/0215107 A1* | 8/2012 | Yamamoto | .......... | G01S 7/52074 |
| | | | | 600/441 |
| 2012/0220871 A1* | 8/2012 | Yamamoto | .......... | G01S 7/52036 |
| | | | | 600/441 |
| 2012/0245468 A1* | 9/2012 | Miyachi | .............. | G01S 7/52049 |
| | | | | 600/447 |
| 2012/0281902 A1* | 11/2012 | Oikawa | ............... | G01S 7/52034 |
| | | | | 382/131 |
| 2013/0060142 A1* | 3/2013 | Ishihara | ................... | A61B 8/14 |
| | | | | 600/447 |
| 2015/0141831 A1* | 5/2015 | Yamamoto | ............... | A61B 8/54 |
| | | | | 600/447 |
| 2015/0196274 A1* | 7/2015 | Yamamoto | .......... | G01S 7/52036 |
| | | | | 600/442 |
| 2015/0320398 A1* | 11/2015 | Honjo | .................. | A61B 8/5207 |
| | | | | 600/447 |
| 2018/0214135 A1* | 8/2018 | Yamamoto | ............... | A61B 8/14 |
| 2019/0209121 A1* | 7/2019 | Miyachi | ................. | G16H 30/40 |
| 2020/0201523 A1* | 6/2020 | Tashiro | ............... | G06F 3/04883 |
| 2020/0214673 A1* | 7/2020 | Yamamoto | .......... | G01S 15/8915 |
| 2020/0337676 A1* | 10/2020 | Kamiyama | .......... | A61B 8/5207 |
| 2020/0397411 A1* | 12/2020 | Noguchi | ............. | G01S 7/52046 |
| 2020/0397412 A1* | 12/2020 | Noguchi | ............... | G01N 29/44 |
| 2021/0113196 A1* | 4/2021 | Imai | ......................... | A61B 8/08 |
| 2021/0137495 A1* | 5/2021 | Noguchi | ............. | A61B 8/4455 |
| 2021/0137496 A1* | 5/2021 | Noguchi | ............. | A61B 8/4472 |
| 2021/0196238 A1* | 7/2021 | Robert | ................. | G01S 7/5205 |
| 2021/0212663 A1* | 7/2021 | Noguchi | ................. | A61B 8/56 |
| 2021/0212664 A1* | 7/2021 | Noguchi | ............. | A61B 8/4472 |
| 2021/0298720 A1* | 9/2021 | Karasawa | ............. | A61B 8/463 |
| 2021/0361261 A1* | 11/2021 | Noguchi | ............. | A61B 8/0841 |
| 2022/0133281 A1* | 5/2022 | Hattori | ................... | A61B 8/462 |
| | | | | 600/440 |
| 2022/0160335 A1* | 5/2022 | Matsumoto | ............ | A61B 8/463 |
| 2022/0175344 A1* | 6/2022 | Matsumoto | ............ | A61B 8/463 |

* cited by examiner

500

502 — Control array to transmit ultrasound energy at first transmit speed

504 — Receive echoes

506 — Determine second transmit speed

508 — Generate multilines based on received echoes

510 — Transmit focus multilines based on second transmit speed

512 — Generate image based on transmit focused multilines

514 — Output image for display

600

602
Determine transmit focus weights

604
Determine transmit focus delays

606
Adjust multilines based on determined transmit focus weights and delays

608
Sum adjusted multilines

RETROSPECTIVE TRANSMIT FOCUSING USING A TRANSMIT SPEED SYSTEMS, DEVICES, AND METHODS

CROSS-REFERENCE TO PRIOR APPLICATIONS

This application is the U.S. National Phase application under 35 U.S.C. § 371 of International Application No. PCT/EP2021/082576, filed on Nov. 23, 2021, which claims the benefit U.S. Provisional Patent Application No. 63/119, 831, filed on Dec. 1, 2020. These applications are hereby incorporated by reference herein.

TECHNICAL FIELD

The present disclosure relates generally to ultrasound imaging and, in particular, to retrospective transmit focusing, which may be used for tissue aberration correction. More specifically, the present disclosure relates to retrospective transmit focusing for an ultrasound transmission based on a transmit speed that may or may not be the same as the transmit speed used for the ultrasound transmission.

BACKGROUND

An ultrasound probe may be configured to transmit ultrasound energy at a particular transmit speed (e.g., a particular speed of sound). However, differences in density and/or other characteristics of imaged mediums may cause the ultrasound energy to propagate through a medium at a different speed (e.g., an actual transmit speed) than the configured transmit speed (e.g., the expected transmit speed). As an illustrative example, ultrasound energy may travel through tissue with low fat content and/or a high density at a relatively higher transmit speed (e.g., 1540 m/s), while ultrasound energy may travel through fattier tissue, such as breast tissue, at a relatively lower transmit speed (e.g., 1480 m/s). Differences between the expected transmit speed used to transmit ultrasound energy and the actual transmit speed that the ultrasound energy travels at within a medium may result tissue aberration. That is, an image generated based on the ultrasound energy may include distortions (e.g., blurriness) resulting from the difference in transmit speeds.

In some cases, the ultrasound probe may be configured for ultrasound transmission at a certain transmit speed based on a transmit pulse pattern. The transmit pulse pattern may be used to actuate transducer elements of the ultrasound probe so that ultrasound energy is transmitted at the desired transmit speed, for example. Configuring the ultrasound probe with a new transmit pulse pattern to affect a desired transmit speed for the transmission of ultrasound energy may be prohibitive in terms of resources (e.g., time, cost, materials, and/or the like). For instance, development and testing required to demonstrate the safety and efficacy of the new transmit pulse pattern may take months.

SUMMARY

Embodiments of the present disclosure relate to retrospective transmit focusing based on a speed of sound that may or may not be the same as a transmit speed used for an ultrasound transmission. For instance, the techniques described herein may be used to transmit focus ultrasound imaging data associated with an ultrasound transmission transmitted at a first transmit speed based on a different, second transmit speed. In particular, an ultrasound imaging system may determine and apply transmit focus weights and/or delays to the ultrasound imaging data based on the second transmit speed. As such the ultrasound imaging system may effectively refocus a transmit beam pattern corresponding to a first transmit speed based on the second transmit speed. In this way, ultrasound data corresponding to a transmission at a particular transmit speed may be tuned to generate an image as though the transmission occurred at a different transmit speed. Accordingly, tissue aberration resulting from differences between the transmission speed at an ultrasound probe and transmission speed through a medium may be reduced, and the use of an ultrasound imaging system configured to transmit ultrasound energy at a particular transmit speed may be expanded to the imaging of tissues having a broader range of characteristics (e.g., corresponding to different ultrasound propagation speeds). To that end, a single transmit pulse pattern may be used across a variety of ultrasound imaging applications, such as breast imaging, vascular imaging, and/or the like. Thus, the usability of an ultrasound imaging system may be improved, and the costs involved with the development and/or implementation of the ultrasound imaging system may be reduced.

In some aspects, an ultrasound imaging system, includes an array of acoustic elements configured to transmit ultrasound energy at a first transmit speed and receive echoes associated with the ultrasound energy transmitted at the first transmit speed. The system further includes a processor circuit in communication with the array of acoustic elements. The processor can be configured to generate a plurality of multilines based on the received echoes, determine a second transmit speed, determine a set of transmit focus delays based on the second transmit speed, adjust the plurality of multilines using the set of transmit focus delays, generate an image based on the adjusted plurality of multilines, and output the generated image to a display in communication with the processor circuit.

In some aspects, the ultrasound imaging system includes a plurality of delay lines in communication with the array of acoustic elements and the processor circuit. The processor circuit may be further configured to control the plurality of delay lines to delay the plurality of multilines according to the set of transmit focus delays to adjust the plurality of multilines.

In some aspects, the processor circuit can be further configured to determine a set of transmit focus weights based on the second transmit speed and to adjust the plurality of multilines using the set of transmit focus weights. In some aspects, the ultrasound imaging system further includes a multiplier in communication with the array of acoustic elements and the processor circuit. Further, the processor circuit can be configured to control the multiplier to apply the set of transmit focus weights to the plurality of multilines to adjust the plurality of multilines.

In some aspects, the ultrasound imaging system includes a summer in communication with the processor circuit and the array of acoustic elements. The summer can be configured to sum the adjusted plurality of multilines to produce transmit focused image data. The processor circuit can be configured to generate the image further based on the transmit focused image data.

In some aspects, the processor circuit can be configured to determine the set of transmit focus delays further based on a model of ultrasound energy transmitted at the second transmit speed.

In some aspects, the array of acoustic elements can be configured to transmit the ultrasound energy with a first focal depth. In such aspects, the processor circuit can be configured to determine the set of transmit focus delays further based on a model of ultrasound energy transmitted with a second focal depth. The processor circuit can be further configured to determine the second focal depth based on the second transmit speed.

In some aspects, the ultrasound energy includes a plurality of ultrasound beams. Further, the array of acoustic elements can be configured to transmit each of the plurality of ultrasound beams from a respective transmit beam location. In some aspects, the plurality of multilines correspond to imaging data associated with a receive line location along which the echoes are received for each of the plurality of ultrasound beams.

In some aspects, the processor circuit can be configured to determine the second transmit speed based on a user input. The user input may include a selection of the second transmit speed from among a set of predetermined transmit speeds.

In some aspects, the processor circuit can be configured to generate the image further based on an additional adjusted plurality of multilines. The adjusted plurality of multilines may correspond to a first line of the image, and the additional adjusted plurality of multilines may correspond to a second line of the image.

In some aspects, the ultrasound imaging system includes the display.

In some aspects, a method of retrospectively transmit focusing ultrasound data for ultrasound imaging includes controlling, by a processor circuit, an array of acoustic elements in communication with the processor circuit to transmit ultrasound energy at a first transmit speed and receive echoes associated with the transmitted ultrasound energy. The method may further include generating, by the processor circuit, a plurality of multilines based on the received echoes. The method may also include determining, by the processor circuit, a second transmit speed and determining, by the processor circuit, a set of transmit focus delays based on the second transmit speed. Further, the method may include adjusting, by the processor circuit the plurality of multilines using the set of transmit focus delays and generating, by the processor circuit, an image based on the adjusted plurality of multilines. The method may further involve outputting, by the processor circuit, the generated image to a display in communication with the processor circuit.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

4

Figure 5:
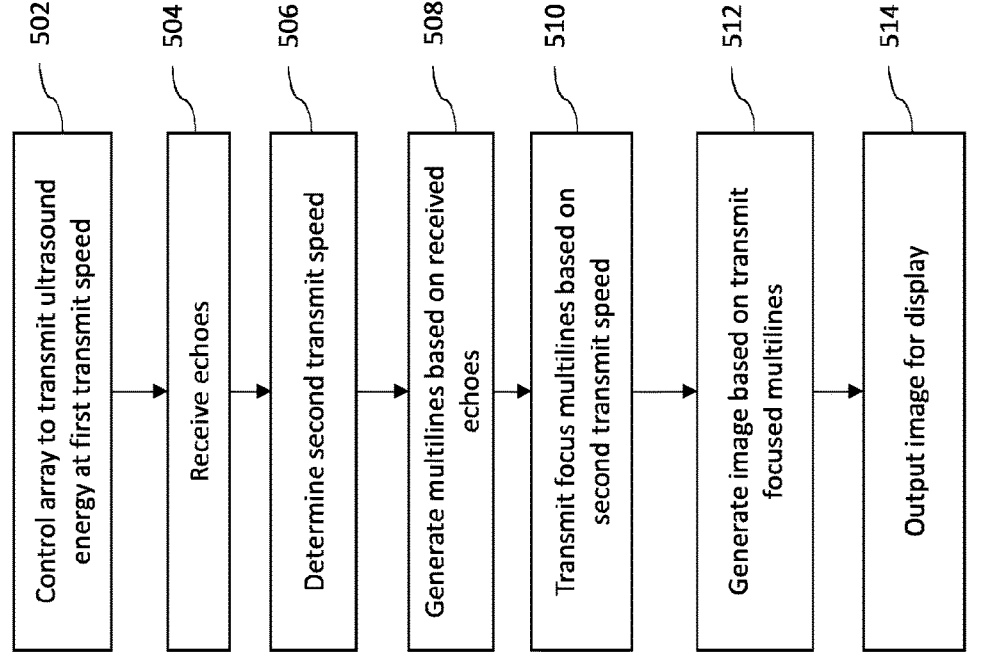

FIG. 5 is a flow diagram of a method of retrospective transmit focusing based on a transmit speed, according to aspects of the present disclosure.

Figure 6:
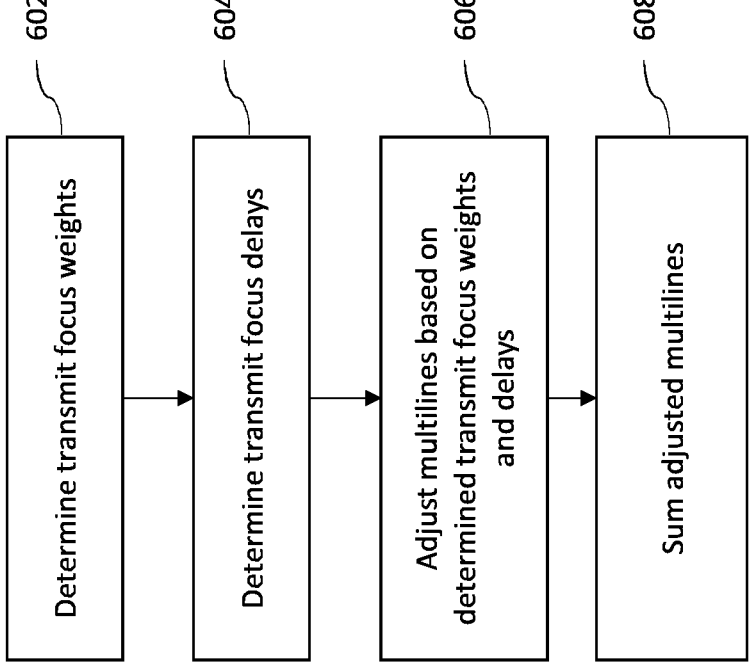

FIG. 6 is a flow diagram of a method of transmit focusing multilines based on a transmit speed, according to aspects of the present disclosure.

Figures 7A, 7B, 7C:
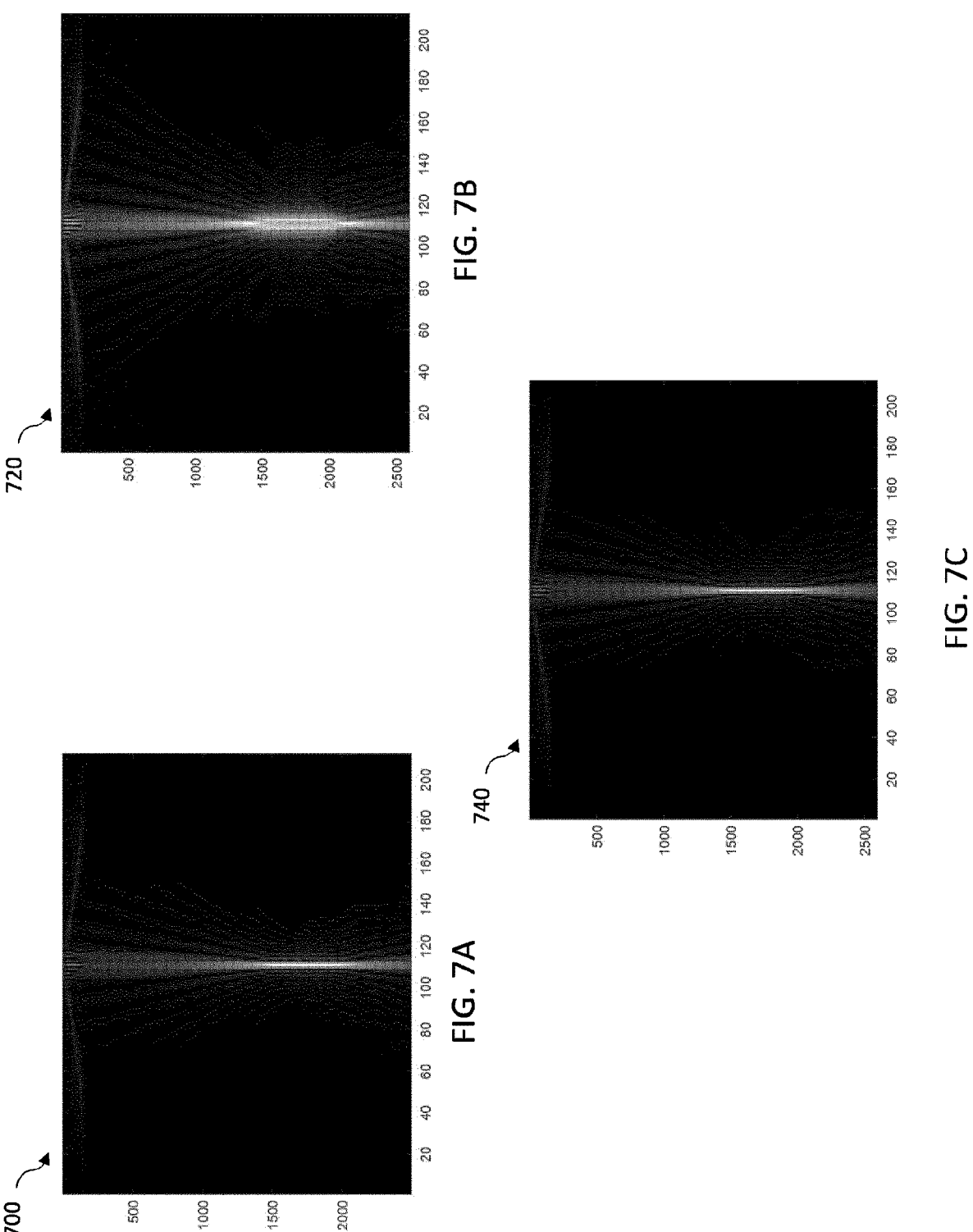

FIG. 7A, FIG. 7B, and FIG. 7C are plots of transmit beam patterns resulting from retrospectively transmit focused ultrasound image data, according to aspects of the present disclosure.

Figure 8:
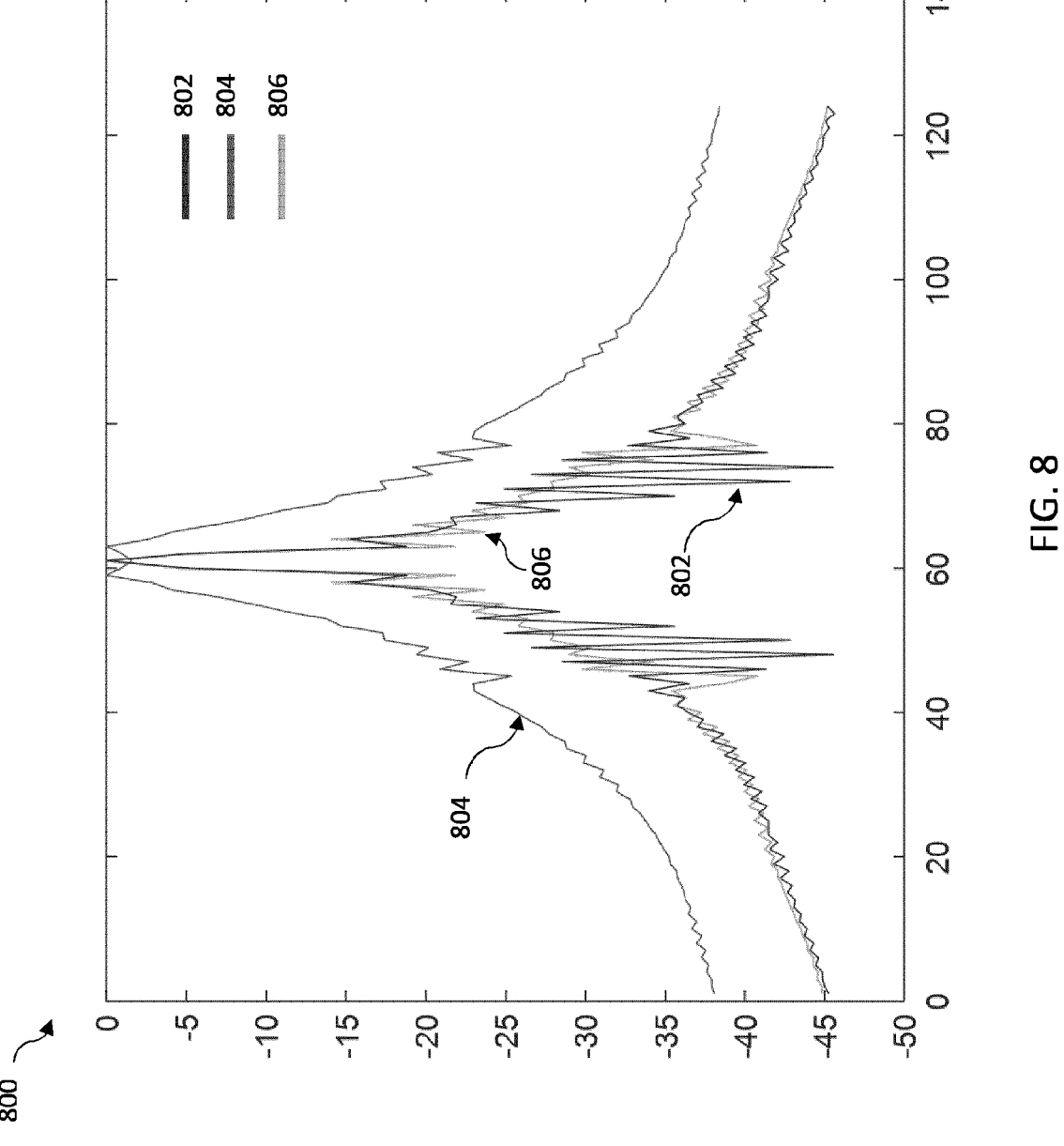

FIG. 8 is a plot of point spread functions, according to aspects of the present disclosure.

Figures 9A, 9B:
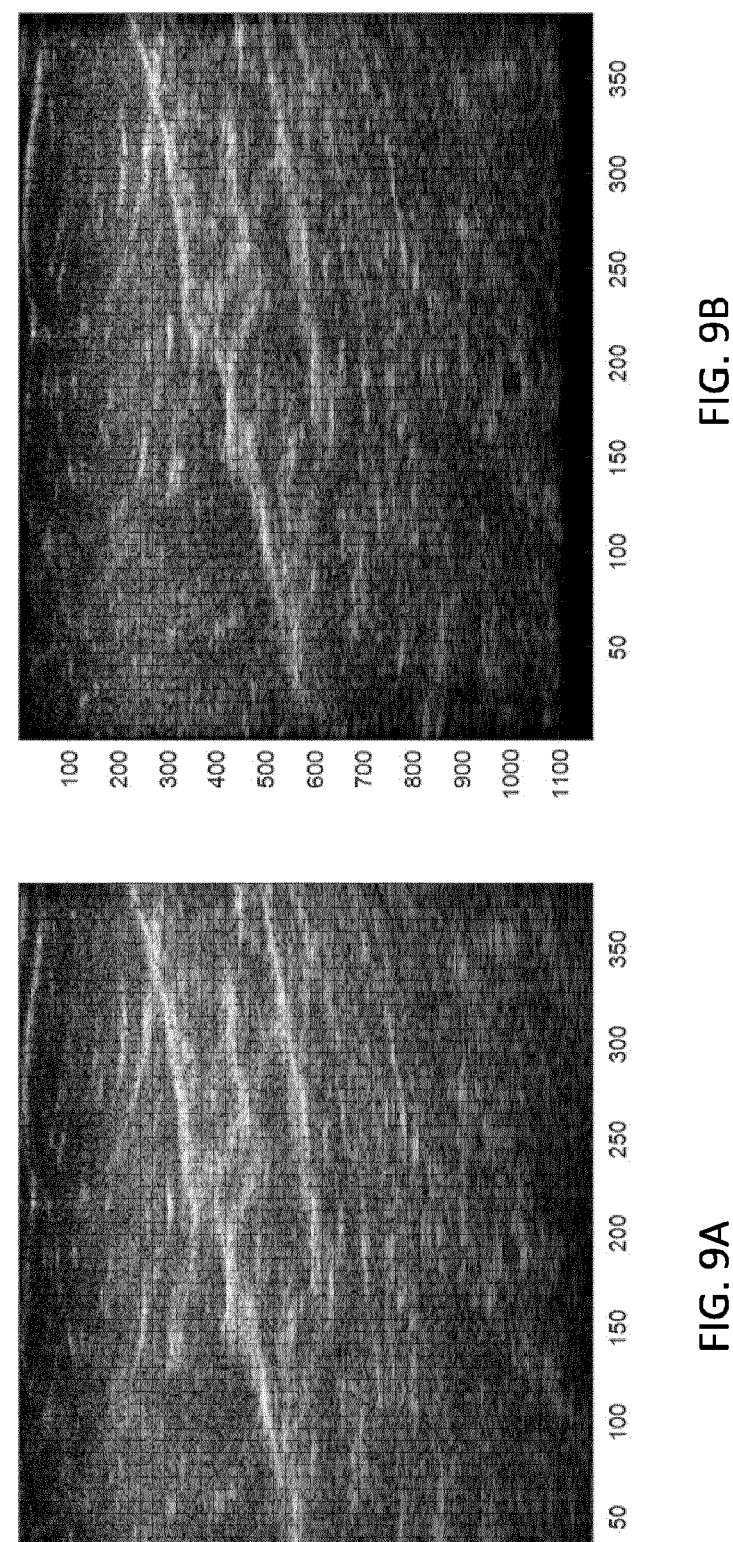

FIGS. 9A and 9B are ultrasound images of breast tissue, according to aspects of the present disclosure.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figures 1A, 1B, 1C:
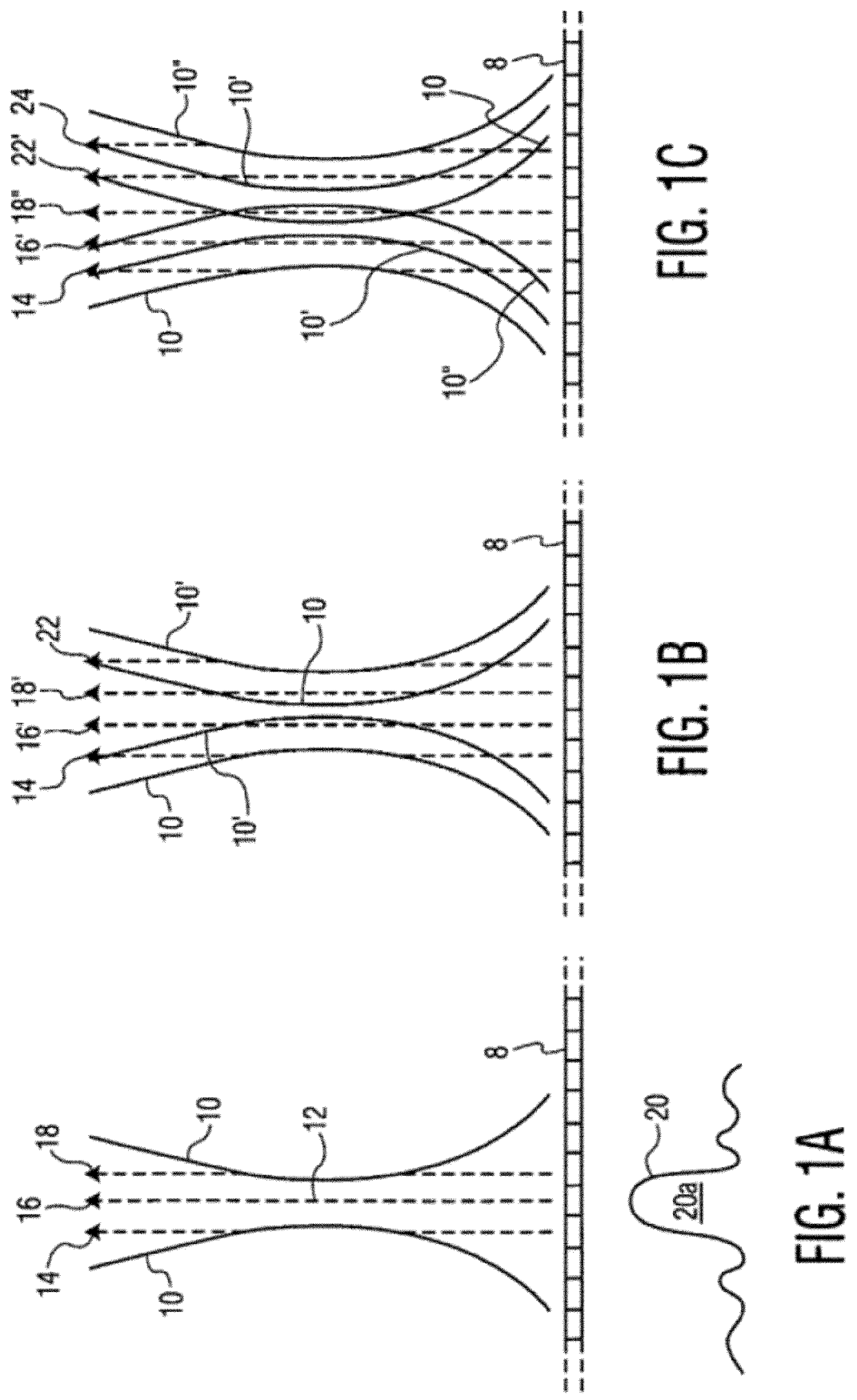
FIGS. 1A, 1B and 1C are diagrammatic views of ultrasound beam transmissions, according to aspect of the present disclosure.

FIGS. 1A-1C illustrate the transmission of ultrasound beams and the corresponding reception of echoes, which may be used to generate multilines. An example of the transmission of ultrasound beams and reception of corresponding echoes for the generation of multilines is described in U.S. Pat. No. 8,137,272, filed Apr. 17, 2007, titled "Ultrasonic Synthetic Transmit Focusing with a Multiline Beamformer," the entirety of which is hereby incorporated by reference. More specifically, FIG. 1A illustrates a profile 10 of a first transmit beam (e.g., an ultrasound beam) transmitted by a transducer array 8, which may be included in an ultrasound probe. FIG. 1A also includes an orthogonal view 20 of the first transmit beam, which illustrates a center lobe 20A and side lobes on either side of the center lobe 20A within the first transmit beam. To that end, the first transmit beam demonstrates a relatively constant power level below the intensity peak at the center of the beam (e.g., the center lobe 20A). In some embodiments, a power level of the beam may be selected (e.g., by a designer) at any suitable level (e.g., 3 dB, 6 dB, 20 dB, and/or the like).

As further illustrated, the first transmit beam includes a focal point 12 at the narrowest width of the profile 10 of the first transmit beam. That is, for example, the first transmit beam may reach its tightest focus at the focal region 12 and subsequently diverge. In some cases, the focal point 12 may correspond to a point at which the first transmit beam is focused by transmit focusing and/or beamforming during transmission of the first transmit beam (e.g., focusing affecting the output at the transducer array 8). As described in greater detail below, the focal point 12 may be extended using the techniques described herein.

The first transmit beam is transmitted with a width that encompasses multiple receive lines 14, 16, and 18. Echoes may be received and focused along the receive line locations 14, 16 and 18 following transmission of the first transmit beam. More specifically, in response to a single transmit beam, the echoes received by the transducer elements of the receive aperture (e.g., within the transducer array 8) are delayed and summed in three different ways to form multiple lines at different line locations 14, 16, and 18, as described in greater detail below. In the illustrated embodiment, receive line 16 is received down the center of the first transmit beam, and receive lines 14 and 18 are laterally steered and focused to be received on either side of the center line (e.g., receive line 16). As further illustrated, the near field and far field portions of the outer lines 14 and 18 are within the profile 10 of the first transmit beam, while a mid-field (e.g., center field) portion of the receive line 14 and the receive line 18 is not included within the profile 10 of the first transmit beam. Accordingly, in some embodiments, echoes and/or portions of echoes within the near field and far field portions may be received along the lines 14 and 18 from transmit energy on either side of the center line position (e.g., corresponding to the receive line 16). To that end, targets in the image field may be sampled on both sides (e.g., corresponding to receive line 14 and 18, respectively) of the center line position. As such, the laterally spread energy of the first transmit beam in the near and far fields may be utilized for efficient image reception and resolution.

FIG. 1B illustrates a profile 10' of a second transmit beam. The second transmit beam may be transmitted by shifting the transmit aperture (e.g., within the transducer array 8) to the right by the spacing of one receive line with respect to the transmit aperture of the first transmit beam. The profile 10' of the second transmit beam may be similar to the profile 10 of the first transmit beam, and while not shown, an orthogonal view of the second transmit beam may be similar to the orthogonal view 20 of the first transmit beam. Accordingly and as in the case of the first transmit beam, the profile 10' of the second transmit beam may accommodate three receive lines 16', 18', and 22. In particular, echoes along the three receive lines 16', 18', and 22 may be simultaneously received and beamformed in response to transmission of the second transmit beam. That is, for example, echoes received by the transducer elements of the receive aperture (e.g., within the transducer array 8) are delayed and summed in three different ways to form multiple lines at different line locations 16', 18', and 22. Because the second transmit beam is transmitted from a shifted aperture with respect to the first transmit beam, receive line 16' is aligned with receive line 16 from the first transmission, receive line 18' is aligned with receive line 18 from the first transmission and receive line 22 is located to the right of the center line 18' of the second transmission.

FIG. 1C illustrates a profile 10" of a third transmit beam. The third transmit beam may be transmitted by shifting the transmit aperture (e.g., within the transducer array 8) to the right by the spacing of one receive line with respect to the transmit aperture of the second transmit beam. The profile 10" of the third transmit beam may be similar to the profile 10 of the first transmit beam and/or the profile 10' of the second transmit beam, and while not shown, an orthogonal view of the third transmit beam may be similar to the orthogonal view 20 of the first transmit beam. The transmit beam profile 10" of the third transmit beam includes at least a portion of three receive lines 18", 22' and 24. To that end, echoes along the three receive lines 18", 22' and 24 may be simultaneously received and beamformed in response to transmission of the second transmit beam. That is, for example, echoes received by the transducer elements of the receive aperture (e.g., within the transducer array 8) are delayed and summed in three different ways to form multiple lines at different line locations 18", 22' and 24. The illustrated receive lines 18", 22", and 24 are spaced from one another with the same spacing as the receive lines 14, 16, and 18, as well as the receive lines 16', 18', and 22. As such, receive line 22' is axially aligned with receive line 22 of the second transmit beam. Further, receive line 18" is axially aligned with receive line 18' of the second transmit beam and receive line 18 of the first transmit beam. Thus, a target in the path of receive lines 18, 18' and 18" may be sampled by three receive lines that each respectively correspond to a different transmit beam (e.g., the first transmit beam, the second transmit beam, and the third transmit beam, respectively). In this way, the echoes corresponding to the first, second, and third transmit beams are co-aligned at the receive lines 18, 18', and 18". The co-aligned echoes may be combined to produce a line of image data along the line of alignment (e.g., corresponding to receive lines 18, 18', and 18"). The line of image data may be focused over a greater depth of field than image data formed using any individual receive line, creating an extended transmit focus effect. In this way, the focusing may be effective over a greater depth of field, as the echo energy from three beam transmissions is combined to produce the resultant image data, as described in greater detail below.

In some embodiments, transmission of ultrasound energy (e.g., ultrasound beams) and reception of corresponding echoes may be repeated (e.g., continued) across the image field in the manner illustrated in FIGS. 1A-C until the full image field has been scanned. Moreover, for a given line location, after echoes for each of the receive lines (e.g., a maximum number of receive lines) corresponding to the location are received, the receive lines for the line location may be processed together (e.g., in parallel). As an illustrative example, the maximum number of receive lines corresponding to a line location illustrated in FIGS. 1A-C is three. Thus, three receive lines corresponding to the same line location, such as 18, 18', and 18", may be received before the receive lines for the line location are processed. After the three receive lines are received, the receive lines may be processed together to produce a line of image data at the corresponding location. To that end, the first set of receive lines (e.g., 14, 16, and 18) corresponding to the first transmit beam and the second set of receive lines 16', 18', and 22 may be stored at least until the third set of receive lines (e.g., 18", 22, and 24) are received. Subsequently, the receive lines 18, 18', and 18" from the first, second, and third set of receive lines, respectively, may be processed together. In this way, the processing of received echoes may not depend on the storage of pre-summed radio-frequency (RF) data from a transmission. Instead, use of storage may be reduced (e.g., minimized) to the storage of sets of receive lines corresponding to a line location before the receive lines for the line location are processed, at which time the storage may be freed up for storage of subsequent receive lines.

While the profiles of the transmit beams illustrated in FIGS. 1A-C are described herein as including three receive lines other suitable numbers of spaced apart, simultaneously received lines, such as, four lines, six lines, eight lines, twelve lines, sixteen lines, and/or the like may be used. In some cases, increasing the number of receive lines received at the transducer array 8 may involve configuring the transducer array to transmit according to a lower F number (e.g., lower F number with respect to an F number corresponding to fewer receive lines) so that ultrasound energy transmitted by the transducer array 8 insonifies a greater expanse of receive line locations. To that end, a wider beam may be produced by transmitting using a smaller transmit aperture. As such, increasing the number of receive lines received at the transducer array 8 may involve decreasing the number of elements of the transducer array 8 used to transmit ultrasound energy. Moreover, while converging transmit beams are illustrated in FIGS. 1A-C, embodiments are not limited thereto. In some embodiments, for example, a diverging transmit beam may be transmitted by the transducer array 8 and focused according to the techniques described herein.

Figure 2:
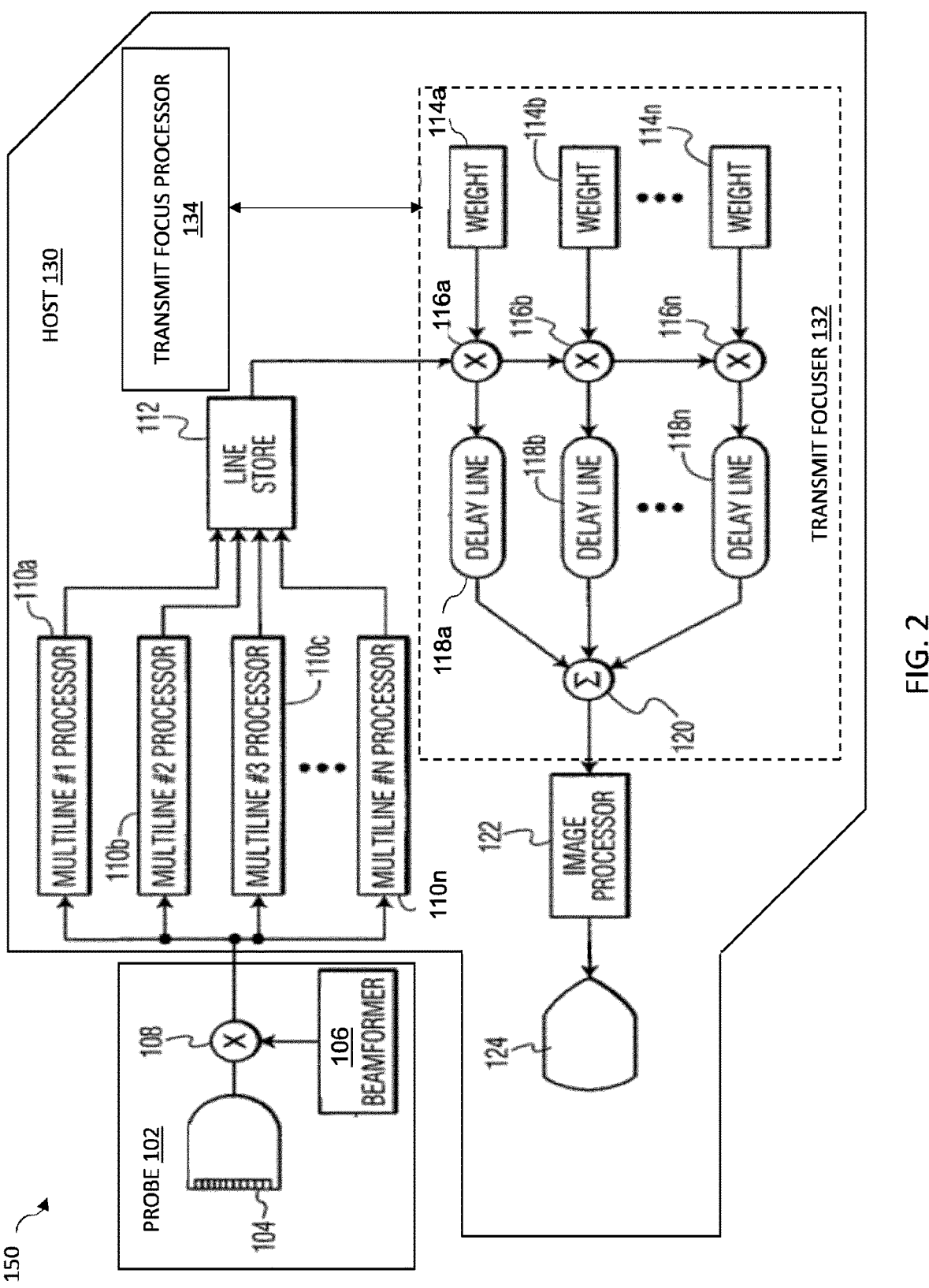
FIG. 2 is a schematic diagram of an ultrasound imaging system, according to aspects of the present disclosure.

Turning now to FIG. 2, a block diagram of an ultrasound imaging system 150 is illustrated, according to aspects of the present disclosure. The system 150 may be used for scanning an area or volume of a patient's body. The system 150 includes an ultrasound imaging probe 102 in communication with a host 130 (e.g., via a communication interface or link). The probe 102 may include a transducer array 104, a transmit beamformer 106, and/or a transmit/receive switch 108 (e.g., a crosspoint switch). The host 130 (e.g., a console) may include multiline processors 110a-110n, a line store 112, transmit focuser 132, a transmit focus processor 134, an image processor 122, and a display 124.

In some embodiments, the probe 102 is an external ultrasound imaging device including a housing configured for handheld operation by a user. The transducer array 104 may be similar to the transducer array 8 of FIG. 1. The transducer array 104 can further be configured to obtain ultrasound data while the user grasps the housing of the probe 102 such that the transducer array 104 is positioned adjacent to or in contact with a patient's skin. The probe 102 is configured to obtain ultrasound data of anatomy within the patient's body while the probe 102 is positioned outside of the patient's body. In some embodiments, the probe 102 can be an external ultrasound probe and/or a transthoracic echocardiography (TTE) probe.

In other embodiments, the probe 102 can be an internal ultrasound imaging device and may comprise a housing configured to be positioned within a lumen of a patient's body, including the patient's coronary vasculature, peripheral vasculature, esophagus, heart chamber, or other body lumen or body cavity. In some embodiments, the probe 102 may be an intravascular ultrasound (IVUS) imaging catheter or an intracardiac echocardiography (ICE) catheter. In other embodiments, probe 102 may be a transesophageal echocardiography (TEE) probe. Probe 102 may be of any suitable form for any suitable ultrasound imaging application including both external and internal ultrasound imaging.

For an ultrasound imaging device, the transducer array 104 emits ultrasound signals towards an anatomical object of a patient and receives echo signals reflected from the object back to the transducer array 104. The ultrasound transducer array 104 can include any suitable number of acoustic elements, including one or more acoustic elements and/or a plurality of acoustic elements. In some instances, the transducer array 104 includes a single acoustic element. In some instances, the transducer array 104 may include an array of acoustic elements with any number of acoustic elements in any suitable configuration. For example, the transducer array 104 can include between 1 acoustic element and 10000 acoustic elements, including values such as 2 acoustic elements, 4 acoustic elements, 36 acoustic elements, 64 acoustic elements, 128 acoustic elements, 500 acoustic elements, 812 acoustic elements, 1000 acoustic elements, 3000 acoustic elements, 8000 acoustic elements, and/or other values both larger and smaller. In some instances, the transducer array 104 may include an array of acoustic elements with any number of acoustic elements in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of acoustic elements (e.g., one or more rows, one or more columns, and/or one or more orientations) can be uniformly or independently controlled and activated. The transducer array 104 can be configured to obtain one-dimensional, two-dimensional, and/or three-dimensional images of a patient's anatomy. In some embodiments, the transducer array 104 may include a piezoelectric micromachined ultrasound transducer (PMUT), capacitive micromachined ultrasonic transducer (CMUT), single crystal, lead zirconate titanate (PZT), PZT composite, other suitable transducer types, and/or combinations thereof.

The object may include any anatomy or anatomical feature, such as blood vessels, nerve fibers, airways, mitral leaflets, cardiac structure, abdominal tissue structure, appendix, large intestine (or colon), small intestine, kidney, liver, and/or any other anatomy of a patient. In some aspects, the object may include at least a portion of a patient's large intestine, small intestine, cecum pouch, appendix, terminal ileum, liver, epigastrium, and/or psoas muscle. The present disclosure can be implemented in the context of any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood vessels, blood, chambers or other parts of the heart, abdominal organs, and/or other systems of the body. In some embodiments, the object may include malignancies such as tumors, cysts, lesions, hemorrhages, or blood pools within any part of human anatomy. The anatomy may be a blood vessel, as an artery or a vein of a patient's vascular system, including cardiac vasculature, peripheral vasculature, neural vasculature, renal vasculature, and/or any other suitable lumen inside the body. In addition to natural structures, the present disclosure can be implemented in the context of man-made structures such as, but without limitation, heart valves, stents, shunts, filters, implants and other devices.

The beamformer 106 is coupled to the transducer array 104. The beamformer 106 controls the transducer array 104, for example, for transmission of ultrasound signals. In such instances, the beamformer 106 is a transmit beamformer. In some embodiments, the transmit beamformer 106 may apply a time-delay to signals sent to individual acoustic transducers within an array in the transducer 104 such that an acoustic signal is steered in any suitable direction propagating away from the probe 102. To that end, selected groups of transducer elements (e.g., acoustic elements) of the transducer array 104 of the ultrasound probe 102 may be actuated at respectively delayed times by the transmit beamformer 106. In this way, the ultrasound probe 102 may be used to transmit ultrasound beams (e.g., ultrasound energy) focused at selected focal regions associated with a respective direction of transmission from a respective origin along the transducer array 104. For instance, the transmit beamformer 106 may actuate different groups of transducer elements (e.g., different transmit apertures) of the transducer array 104 so that the ultrasound probe 102 transmits the first, second, and third beams illustrated in FIGS. 1A-C and corresponding to the profiles 10, 10', and 10", respectively. In some instances, the beamformer 106 can be a receive beamformer and control reception of ultrasound echoes at the transducer array 104. The receive beamformer 106 may include multiple stages of beamforming.

As illustrated, the beamformer 106 may be coupled to the transducer array 104 by a transmit/receive switch 108. The first transmit/receive switch 108 may include a crosspoint switch. Moreover, the transmit/receive switch 108 may be implemented to direct high voltage transmit pulses from the transmit beamformer 106 and/or signals from the host 130 to the ultrasound probe 102 and to direct ultrasound echoes and/or signals from the ultrasound probe 102 to the host 130. As such, the transmit/receive switch 108 may protect circuitry within the ultrasound probe 102 and/or the host 130 used for reception, which may include circuitry configured for operation at a lower voltage, from the higher voltage of transmit pulses.

In response to each transmit beam, the ultrasound probe 102 may receive echoes (e.g., at the transducer array 104), and the host 130 may receive the echoes and/or signals associated with the echoes from the ultrasound probe 102. At the host 130, the echoes received from the ultrasound probe 102 may be applied to the inputs of multiline processors 110*a-n*. The multiline processors 110*a-n* may also be described as processor circuits, which can include other components in communication with the multiline processors 110*a-n*, such as a memory. The multiline processors 110*a-n* may include a central processing unit (CPU), a graphical processing unit (GPU), a digital signal processor (DSP), an application specific integrated circuit (ASIC), a controller, a field programmable gate array (FPGA) device, another hardware device, a firmware device, or any combination thereof configured to perform the operations described herein. The multiline processors 110*a-n* may also be implemented as a combination of computing devices, e.g., a combination of a DSP and a microprocessor, a plurality of microprocessors, one or more microprocessors in conjunction with a DSP core, or any other such configuration.

Further, the multiline processors 110*a-n* may be configured to process ultrasound echoes. For example, the multiline processors 110*a-n* may each include a receive beamformer configured to apply a respective set of delays to the received echoes. In some embodiments, the multiline processors 110*a-n* provide a first or only stage of receive beamforming. In other embodiments, multiline processors 110*a-n* provide a second or subsequent stage of receive beamforming (e.g., when a first stage of receive beamforming is performed by the beamformer 106). The receive beamformers may also apply apodization weights to the echoes received from the transducer array 104 elements. As a result of the applied set of delays and/or apodization weights, the multiline processors 110*a-n* may form differently steered receive beams corresponding to the same transmit beam. More specifically, the multiline processors 110*a-n* may produce the multilines (e.g., multiline echoes), which correspond to echoes received along different receive lines for a given transmit beam. For instance, the multiline processors 110*a-n* may produce multilines corresponding to receive lines 14, 16, and 18 (FIG. 1A), respectively, for the first transmit beam, multilines corresponding to receive lines 16', 18', and 22 (FIG. 1B), respectively, for the second transmit beam, and multilines corresponding to the receive lines 18", 22', and 24 (FIG. 1C), respectively, for the third transmit beam.

The multilines generated at the multiline processors 110*a-n* may be output to the line store 112. The line store 112 may include memory and/or storage, such as one or more registers, and may store multilines at least until each of the multilines corresponding to a particular receive line (e.g., needed to form a line of within an image) have been acquired. For instance, for an image line corresponding to receive line locations 18, 18', and 18", the line store 112 may store the first set of multilines corresponding to the first transmit beam and receive line locations 14, 16, and 18, as well as the second set of multilines corresponding to the second transmit beam and receive line locations 16', 18', and 22, at least until the third set of multilines corresponding to the third transmit beam and receive lines 18", 22', and 24 is received, as described above.

After each of the multilines corresponding to a particular image line are received at the line store 112, the line store 112 may output the multilines corresponding to the receive line to a transmit focuser 132. As illustrated, the transmit focuser 132 may include weights 114*a-n*, multipliers 116*a-n*, delay lines 118*a-n*, and a summer 120. In some embodiments, the quantity of each of the weights 114*a-n*, the multipliers 116*a-n*, and the delay lines 118*a-n* may correspond to the number of multiline processors 110*a-n*, which, in turn, may correspond to the quantity of receive line locations (e.g., the quantity of multilines) generated for a particular line of an image. Further, the transmit focuser 132 may be implemented as a combination of software components and/or hardware components. Moreover, the transmit focuser 132 may be implemented as a combination of analog and/or digital components. For instance, the delay lines 118*a-n* may be implemented as digital delay lines by storing the data (e.g., multiline data) in memory and reading the data out at a later time corresponding to a desired delay. Additionally or alternatively, the delay lines 118*a-n* may be implemented with shift registers of differing lengths and/or clock signals. In some embodiments, the delay lines 118*a-n* may be implemented with an interpolating beamformer. Similarly, the summer 120 may be implemented with adder circuitry and/or as a digital adder.

In some embodiments, the transmit focuser 132 may apply respective apodization weights to each of the multilines in a group of multilines corresponding to a particular line of an image (e.g., in the group of multilines received from the line store 112). In particular, the multipliers 116*a-n* may each receive a multiline of the group of multilines and a corresponding transmit focus weight of the weights 114*a-n* as inputs and may output an adjusted multiline (e.g., a weighted multiline). In some embodiments, the weights 114*a-n* may be configured to weight each multiline as a function of the round-trip impulse response associated with the multiline. Moreover, the weights 114*a-n* may be configured by a transmit focus processor 134, as described in greater detail below.

The transmit focuser 132 may additionally or alternatively delay the multilines received from the line store 112. For instance, using the delay lines 118*a-n*, the transmit focuser 132 may apply respective delays to each of the multilines in the group of multilines corresponding to a particular line of an image. The delays may equalize phase shift variance that exists from line to line for the multilines with differing transmit-receive beam location combinations. As such, signal cancellation caused by phase differences of the combined multilines may be minimized and/or avoided. To that end, the delay applied by a delay line 118 may depend on the location of the multiline and/or receive line in relation to the center of the corresponding transmit beam. As an illustrative example and with respect to the first transmit beam illustrated in FIG. 1A, the delay applied to a multiline associated with the receive line location 18 may depend on the distance of the receive line location from the receive line location 16

(e.g., the center of the first transmit beam). Further, the delays effected by the delay lines 118a-n may be configured by the transmit focus processor 134, as described in greater detail below.

The transmit focuser 132 may further be configured to sum the adjusted (e.g., weighted and/or delayed multilines) at the summer 120. In particular, the summer 120 may sum (e.g., combine) each adjusted multiline in the group of multilines corresponding to a particular line of an image. The output of the summer 120 and/or the transmit focuser 132 may be coupled to the image processor 122. As such, the image processor may receive the combined adjusted multilines. The image processor 122 may then generate an image based on the combined adjusted multilines. Further, the image processor 122 may perform scan conversion or other processing to improve the generated image. The resultant image may be output for display at the display 124.

As discussed above, the transmit focuser 132 may be in communication with the transmit focus processor 134, which may configure the weights 114a-n and/or the delay lines 118a-n. The transmit focus processor 134 may also be described as a processor circuit. The transmit focus processor 134 may include a central processing unit (CPU), a graphical processing unit (GPU), a digital signal processor (DSP), an application specific integrated circuit (ASIC), a controller, a field programmable gate array (FPGA) device, another hardware device, a firmware device, or any combination thereof configured to perform the operations described herein. The transmit focus processor 134 may also be implemented as a combination of computing devices, e.g., a combination of a DSP and a microprocessor, a plurality of microprocessors, one or more microprocessors in conjunction with a DSP core, or any other such configuration.

In some embodiments, the transmit focus processor 134 may configure the weights 114a-n and/or configure the multipliers 116a-n to apply the weights 114a-n based on a weighting algorithm. For instance, the weight to be applied to a multiline may be determined as shown below:

$$\text{Weight}(X,Z)=\text{amplitude}(X,Z), \tag{1}$$

where X represents the azimuth of the received multiline with respect to the beam axis of the corresponding transmit beam, where X=0 corresponds to the center axis of the transmit beam, and Z represents a depth at which the multiline forms a point of an image. Further, the amplitude (X, Z) represents the insonification amplitude by the transmit wave-front (e.g., wave-front of the transmit beam) at a point in the image field. By varying the weights as a function of depth (e.g., according to equation 1), the transmit processor 134 may retrospectively and dynamically vary the size and shape (apodization) of the transmit aperture with depth. That is, for example, the transmit processor 134 may vary the size and shape of the transmit aperture after the transmit beam is transmitted at the ultrasound probe 102.

The transmit focus processor 134 may configure the delay lines 118a-n (e.g., the delay affected by the delay lines) based on a delay algorithm. For instance, the delay applied to a multiline by a delay line 118 may be determined as shown below:

$$\text{Delay}(X,Z)=\text{propagation\_time}(X,Z)-\text{propagation\_time}(0,Z), \tag{2}$$

where X represents the azimuth of the received multiline with respect to the beam axis of the corresponding transmit beam, where X=0 corresponds to the center axis of the transmit beam, and Z represents a depth at which the multiline forms a point of an image. Further, the propagation_time (X, Z) represents the propagation time for a transmit wave-front to reach a point represented by X and Z, and propagation_time (0, Z) represents the time to reach a point at the same depth but on-axis (e.g., on the center axis of the transmit beam).

In some embodiments, the transmit focus processor 134 may determine the result of the weighting algorithm (e.g., equation 1) and/or the delay algorithm (e.g., equation 2) based on simulation (e.g., a model) of a transmit field. In particular, the transmit focus processor 134 may determine values of the function amplitude (X, Z) and/or the function propagation_time(X, Z) based on the simulation. For instance, using monochromatic simulation at several frequencies, the transmit focus processor 134 may determine the propagation time based on phase delay of the transmit field. Further the transmit focus processor 134 may determine the amplitude based on averaging the amplitude of the transmit field at several simulated frequencies. In some embodiments, the transmit focus processor 134 may then apply a depth-dependent normalization to the weights 114a-n. The normalization may multiply each weight at a given depth by a common factor. In some cases, the normalization may be selected so that speckle regions have uniform brightness with depth.

By configuring the delay lines 118a-n based on the delay algorithm (equation 2) and/or the multipliers 116a-n and/or weights 114a-n based on the weighting algorithm (equation 1), the transmit focus processor may configure the transmit focuser 132 to retrospectively transmit focus transmit beams transmitted by the ultrasound probe 102. That is, for example, the transmit focus processor may configure the delay lines 118a-n so that the delay lines 118a-n, along with the summer 120, refocus the multilines that are co-aligned in a given direction. Such refocusing may account for phase differences resulting from the use of different transmit beam locations for each multiline. As a result, the refocusing may minimize or prevent undesired phase cancellation in the combined multilines. Further, the weights 114a-n may weight the contributions of the multilines in relation to their respective proximity to a corresponding transmit beam. For instance, the transmit focus processor 134 may, based on the weighting algorithm (e.g., equation 1) and one or more simulations of the transmit field, configure the weights 114a-n so that higher weights are applied to multilines with higher signal-to-noise ratios. As a result, the image generated and output to the display 124 may include an extended depth of field (e.g., an extended focus with respect to the focal point 12 resulting from conventional focusing) along each receive line and an enhanced penetration (e.g., improved signal-to-noise ratio) due to the combination of multiple samplings in each receive line direction.

In some embodiments, the transmit focus processor 134 may derive the delays for the configuration of the delay lines 118a-n and/or the weights for the configuration of the weights 114a-n based on simulations of a transmit field that model the transmit characteristics of the beams transmitted by the ultrasound probe 102. These characteristics may include, for example, the speed of sound used to transmit the transmit beams, the size and/or shape of the transmit aperture (e.g., the number and/or location of transducer elements in the transducer array 104 used to transmit the transmit beams), the focal depth of the transmit beams, and/or the like. In some embodiments, the transmit processor 134 may, during simulation of the transmit field, alter one or more of these characteristics in comparison with the values used during transmission. For instance, the transmit processor 134 may use a different speed of sound to determine the delays for the configuration of the delay lines 118*a-n* and/or the weights for the configuration of the weights 114*a-n* than the speed of sound used by the ultrasound probe 102 for transmission of transmit beams. In this way, the transmit focuser 132 may transmit focus multilines based on a different speed of sound than the speed of sound used for ultrasound transmission, which may correct for differences between an expected speed of sound corresponding to a speed of sound setting at the ultrasound probe 102 and an actual speed of sound resulting from propagation of ultrasound energy through a particular medium. That is, for example, the transmit focusing based on the actual speed of sound may be used to perform tissue aberration correction (TAC), as described in greater detail below.

While the ultrasound imaging system 150 is illustrated and described as having certain components included in the ultrasound probe 102 and certain components included in the host 130, embodiments are not limited thereto. To that end, in some embodiments, the display 124 may be a stand-alone device in communication with the host 130. Further, in some embodiments, the beamformer 106 and/or the switch may additionally or alternatively be included in the host 130. In some embodiments, the multiline processors 110*a-n* may be included in the ultrasound probe 102. Moreover, while certain components are illustrated as separate, it may be appreciated that one or more components may be included in a combined system and/or that a certain component may perform one or more of the techniques described herein.

In some embodiments, the processors 110*a-n*, 134, and/or 122 may each be a part of a combined system (e.g., the host 130). For example, in some embodiments, the processors 110*a-n*, 134, and/or 122 may be positioned within the same enclosure or housing. In addition, the processors 110*a-n*, 134, and/or 122 may share one or more software or hardware components. To that end, one or more of the processors 110*a-n*, 134, and/or 122 may be implemented as a single processing system. In other embodiments, the processors 110*a-n*, 134, and/or 122 may be separate systems but may be in communication with one another. The processors may be in continuous communication with one another or may be in intermittent communication with one another. The processors may be in communication with one another or with the ultrasound probe 102, the display 124, the transmit focuser 132, and/or the like via one or more wired connecting cables including any suitable conductors, such as single conductors, twisted pairs, universal serial bus (USB) cables, or any other suitable connecting cables. The processors 110*a-n*, 134, and/or 122 may additionally or alternatively be in communication with one another and/or another component of the ultrasound imaging system 150 via a wireless connection, an optical connection, or may be in connection via any suitable type of movable memory or storage media, or via any other suitable means of communication. Any and/or all of the processors 110*a-n*, 134, and/or 122 may include or be a part of any suitable system or device such as, but not limited to, a mobile console, a desktop computer, laptop computer, tablet, smartphone, or any other suitable computing device.

Figure 3:
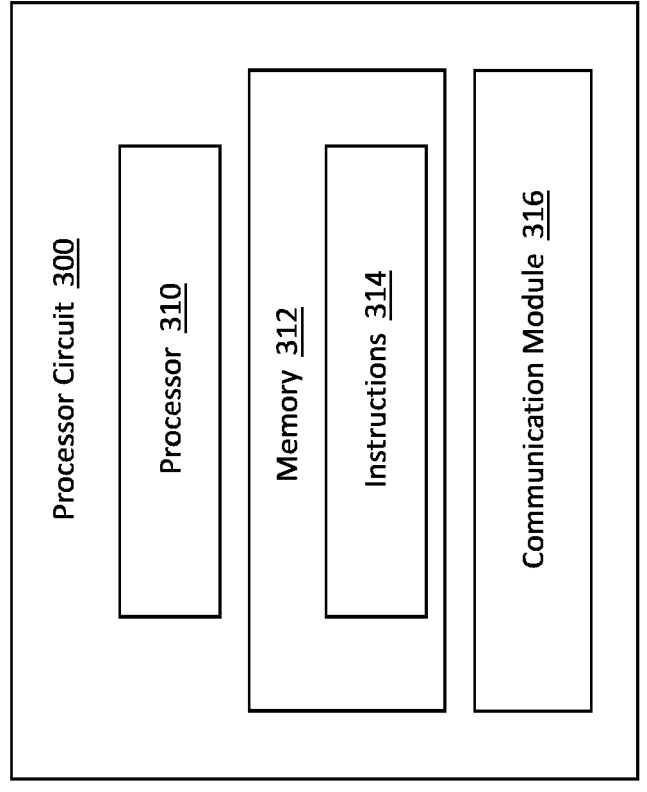
FIG. 3 is a schematic diagram of a processor circuit, according to aspects of the present disclosure.

FIG. 3 is a schematic diagram of a processor circuit 300, according to aspects of the present disclosure. The processor circuit 300 or a similar processor circuit may be implemented in any suitable device or system previously disclosed. One or more processor circuits 300 can be configured to perform the operations described herein. The processor circuit 300 can include additional circuitry or electronic components, such as those described herein. In an example, one or more processor circuits 300 may be in communication with the transducer array 104, the beamformer 106, circuitry, or other components within the ultrasound probe 102. Further, one or more processor circuits 300 may be in communication with the line store 112, the transmit focuser 132, circuitry, or other components within the host 130. One or more processor circuits 200 may also be in communication with the display 124, as well as any other suitable component or circuit within the ultrasound imaging system 150. Moreover, any of the host 130, and/or the processors 110*a-n*, 134, and/or 122 may be similar to the processor circuit 300. As shown, the processor circuit 300 may include a processor 310, a memory 312, which may include instructions 314, and a communication module 316. These elements may be in direct or indirect communication with each other, for example via one or more buses.

The processor 310 may include a CPU, a GPU, a DSP, an application-specific integrated circuit (ASIC), a controller, a field programmable gate array (FPGA), another hardware device, a firmware device, or any combination thereof configured to perform the operations described herein. The processor 310 may also be implemented as a combination of computing devices, e.g., a combination of a DSP and a microprocessor, a plurality of microprocessors, one or more microprocessors in conjunction with a DSP core, or any other such configuration.

The memory 312 may include a cache memory (e.g., a cache memory of the processor 310), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 312 includes a non-transitory computer-readable medium. The memory 312 may store instructions 314. The instructions 314 may include instructions that, when executed by the processor 310, cause the processor 310 to perform the operations described herein with reference to the multiline processors 110*a-n*, the transmit focus processor 134, the image processor 122, and/or the like. Instructions 314 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 316 can include any electronic circuitry and/or logic circuitry to facilitate direct or indirect communication of data between the processor circuit 300, the components of the host 130, components of the ultrasound probe 102, and/or the display 124. In that regard, the communication module 316 can be an input/output (I/O) device. For instance, the communication module 316 may include a touch sensitive pad or touch screen display, keyboard/mouse, joystick, button, scroll wheel, and/or the like. In some instances, the communication module 316 facilitates direct or indirect communication between various elements of the processor circuit 300 and/or the devices and systems of the ultrasound imaging system 150. Moreover, the communication module 316 may facilitate wireless and/or wired communication between various elements of the processor circuit 300 and/or the devices and systems of the ultrasound imaging system 150 using any suitable communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G.

Figures 4A, 4B:
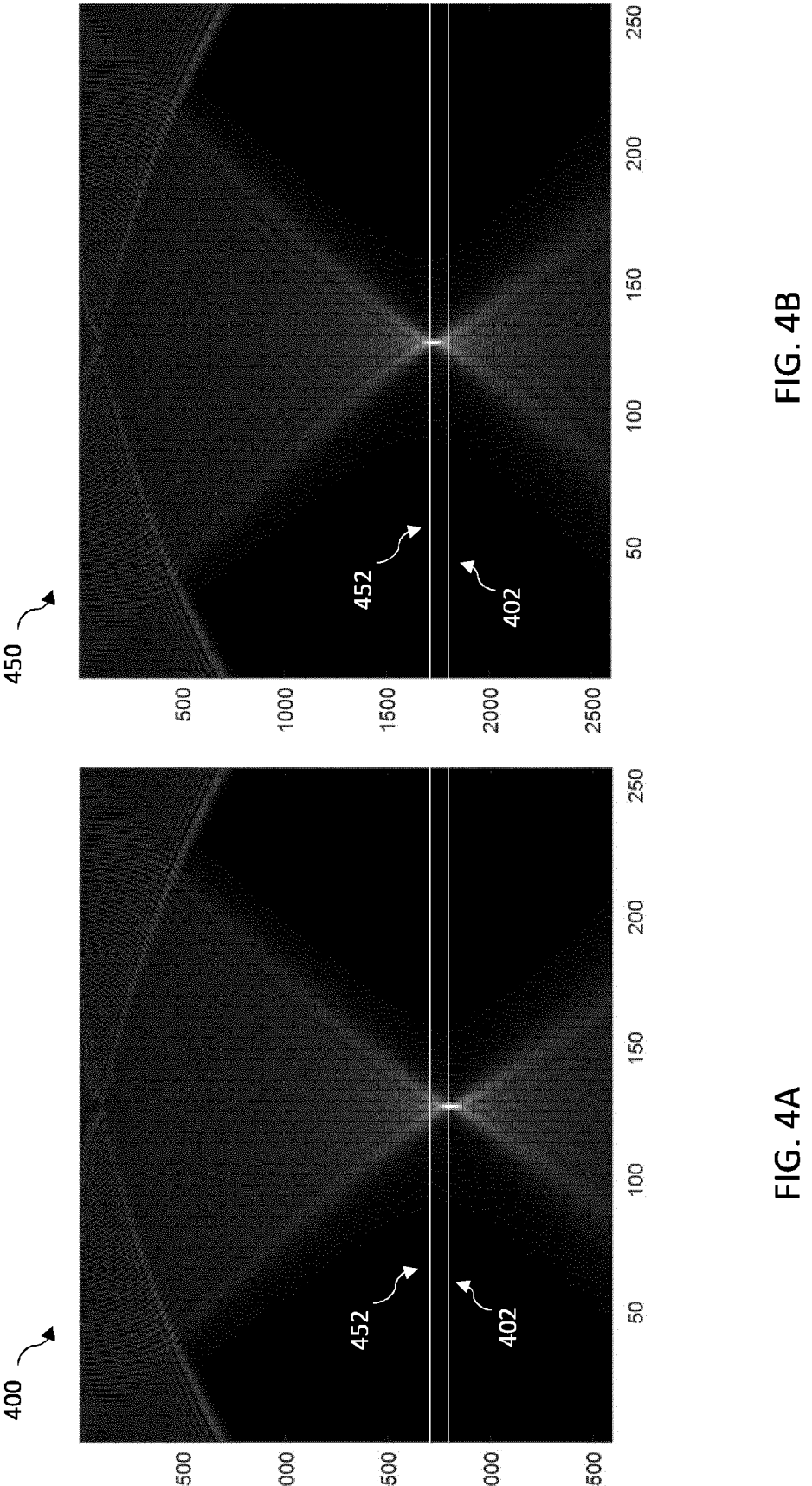
FIG. 4A and FIG. 4B are plots of simulated transmit beam patterns, according to aspects of the present disclosure.

Turning now to FIGS. 4A-B, simulated transmit beam patterns. In FIGS. 4A-B, the horizontal axis represents azimuth in some arbitrary units, and the vertical axis represents depth in some arbitrary units. Each of plot 400 of FIG. 4A and plot 450 illustrates a respective simulated transmit beam pattern for ultrasound energy travelling through a medium. In the case of the plot 400, the transmit beam pattern corresponds to the transmission of the ultrasound energy from an ultrasound probe (e.g., ultrasound probe 102) at the transmit speed of 1540 meters/second (m/s). The plot 450 illustrates a transmit beam pattern corresponding to the transmission of the ultrasound energy from the ultrasound probe at the transmit speed of 1480 m/s.

In some embodiments, for example, an ultrasound probe, such as the ultrasound probe 102, may be configured (e.g., via the beamformer 106) to transmit ultrasound energy at a particular transmit speed, such as the transmit speed 1540 m/s illustrated in FIG. 4A or the transmit speed 1480 m/s illustrated in FIG. 4B. For instance, the beamformer 106 may actuate elements of the transducer array 104 with a transmit pulse pattern corresponding to a desired transmit speed. To that end, the beamformer may actuate elements of the transducer array 104 with a first transmit pulse pattern for ultrasound transmissions at 1540 m/s and may actuate elements of the transducer array 104 with a different, second transmit pulse pattern for ultrasound transmissions at 1480 m/s. While the ultrasound may be configured to transmit ultrasound energy at a particular transmit speed (e.g., an expected transmit speed), due to differences in density and/or other characteristics of a medium, the ultrasound energy may propagate through the medium at a different speed (e.g., an actual transmit speed). As an illustrative example, ultrasound energy may travel through tissue with low fat content and/or a high density at a relatively higher transmit speed (e.g., 1540 m/s), while ultrasound energy may travel through fattier tissue, such as breast tissue, at a relatively lower transmit speed (e.g., 1480 m/s).

In the embodiments illustrated in FIGS. 4A-B, the medium may have an ultrasound propagation speed of 1480 m/s. As such, while the plot 400 corresponds to ultrasound energy transmitted at the transmit speed 1540 m/s (e.g., with an expected transmit speed of 1540 m/s), the ultrasound energy may propagate through the medium at the transmit speed of 1480 m/s (e.g., at the actual transmit speed of 1480 m/s). In this way, the plot 400 illustrates an example of a transmit beam pattern having a mismatch between the actual transmit speed of ultrasound energy within the medium and the expected transmit speed used during transmission at the ultrasound probe. The plot 450, on the other hand, illustrates an example of a transmit beam pattern where the actual transmit speed of ultrasound energy within the medium approximately matches the expected transmit speed used during transmission at the ultrasound probe.

The focal depth 402 corresponds to the focal depth of the transmit beams corresponding to the expected transmit speed of 1540 m/s (e.g., the focal depth of plot 400), and the focal depth 452 corresponds to the focal depth of the transmit beams corresponding to the expected transmit speed of 1480 m/s (e.g., the focal depth of plot 450). As illustrated, the focal depth 402 is less than the focal depth 452. To that end, FIGS. 4A-B illustrate that a mismatch between the actual transmit speed of the ultrasound energy within the medium and the expected transmit speed used during transmission of the ultrasound energy at the ultrasound probe 102 may associated with a shift (e.g., an offset) in the focal depth of the resulting transmit beam pattern. In some cases, this shift may cause image distortion (e.g., blurring and/or lowered image resolution) in an image resulting from the ultrasound energy. This shift in focal depth and/or the resulting image distortion may be referred to as tissue aberration.

As an illustrative example, tissue aberration may occur when the host and/or ultrasound probe are not configured with a transmit pulse pattern corresponding to the speed at which the ultrasound energy propagates through the medium. Configuring the ultrasound host and/or the ultrasound probe with a new transmit pulse pattern to affect a desired transmit speed for the transmission of ultrasound energy may be prohibitive in terms of resources (e.g., time, cost, materials, and/or the like). For instance, development and testing required to demonstrate the safety and efficacy of the new transmit pulse pattern may take months. Accordingly, alternative methods of tissue aberration correction (TAC) may improve the usability of an ultrasound imaging system and may reduce costs involved with the development and/or implementation of the ultrasound imaging system.

As described in greater detail below, the ultrasound imaging system 150 may be used for tissue aberration correction and/or to retrospectively transmit focus ultrasound imaging data based on a different transmit speed than the transmit speed used during an ultrasound transmission. In particular, the ultrasound imaging system 150 may be used to transmit focus ultrasound imaging data associated with an ultrasound transmission at a first transmit speed based on a different, second transmit speed. For instance, the ultrasound imaging system 150 may determine and apply transmit focus weights and/or delays to multilines associated with the ultrasound transmission based on the second transmit speed. As such the ultrasound imaging system 150 may effectively refocus a transmit beam pattern corresponding to a first transmit speed based on the second transmit speed. In this way, ultrasound data corresponding to a transmission at a particular transmit speed may be tuned to generate an image as though the transmission occurred at a different transmit speed. Accordingly, tissue aberration resulting from differences between the transmission speed at an ultrasound probe and transmission speed through a medium may be reduced, and the use of an ultrasound imaging system configured to transmit ultrasound energy at a particular transmit speed may be expanded to the imaging of tissues having a broader range of characteristics (e.g., corresponding to different ultrasound propagation speeds).

FIG. 5 is a flow diagram of a method 500 of retrospective transmit focusing based on a different transmit speed than the transmit speed used at an ultrasound probe (e.g., ultrasound probe 102) to transmit ultrasound energy, according to aspects of the present disclosure. One or more steps of the method 500 will be described with reference to FIG. 6. As illustrated, the method 500 includes a number of enumerated steps, but embodiments of the method 500 may include additional steps before, after, or in between the enumerated steps. In some embodiments, one or more of the enumerated steps may be omitted, performed in a different order, or performed concurrently. The steps of the method 500 can be carried out by any suitable component within the ultrasound imaging system 150 and all steps need not be carried out by the same component. In some embodiments, one or more steps of the method 500 can be performed by, or at the direction of, a processor circuit (e.g., the processor circuit 300 (FIG. 3)) of the ultrasound imaging system 150, including the host 130, the transmit focus processor 134, the image processor 122, or any other component.

At step 502, the method 500 includes controlling an array to transmit ultrasound energy at a first transmit speed. For instance, the host 130 may control the transducer array 104 to output the ultrasound energy at a first transmit speed, in accordance with a transmit pulse pattern. More specifically, the host 130 may communicate to the beamformer 106, which, in response to the communication, may actuate one or more transducer elements of the transducer array 104 according to the transmit pulse pattern. As a result, the actuated one or more transducer elements may transmit the ultrasound energy at the first transmit speed.

In some embodiments, the first transmit speed may be a default transmit speed of the ultrasound probe 102 and/or the host 130. For instance, the ultrasound probe 102 may be preconfigured for transmission of the ultrasound energy at the first transmit speed and/or the host 130 may be preconfigured to control the ultrasound probe 102 to transmit the ultrasound energy at the first transmit speed. For instance, the host 130 may be preconfigured with the transmit pulse pattern corresponding to the first transmit pattern. Moreover, in some cases, the first transmit speed may be the only transmit speed that the ultrasound probe 102 and/or the host 130 are configured to use. Additionally or alternatively, the host 130 may determine the first transmit speed based on a user input received at the host 130 via the communication module 316. In some embodiments, for example, the host 130 may be preconfigured with a number of transmit pulse patterns corresponding to a respective set of predetermined transmit speeds. In such cases, the user input may select a transmit speed from the set of predetermined transmit speeds, and based on the selection, the host 130 may select the transmit pulse pattern for controlling the ultrasound probe 102. As an illustrative example, the first transmit speed may be 1540 m/s.

At step 504, the method 500 involves receiving echoes. In particular, the ultrasound probe 102 may receive echoes associated with the ultrasound energy transmitted at the first speed. For instance, after transmitting the ultrasound energy at the first transmit speed, the ultrasound probe 102 may control operation of the transducer array 104 to receive the echoes, and the transmit/receive switch 108 may route signals associated with the received echoes (e.g., electrical signals corresponding to the received echoes) to the host 130.

At step 506, the method 500 involves determining a second transmit speed. In some embodiments, the host 130 may determine the second transmit speed based on a user input. For instance, the host 130 may receive the user input via the communication module 316, which may include an I/O device, as described above. To that end, the user input may be received via interaction with a graphical user interface (GUI), a touchscreen interface, a button, a mouse, a keyboard, a joystick, a trackpad, and/or the like. Moreover, the user input may correspond to a selection of the second transmit speed. For instance, the user input may select the second transmit speed from among a set of transmit speeds predetermined and/or preconfigured at the host 130. For instance, the host 130 may include a two or more transmit speeds, and each transmit speed may correspond to a different type of tissue. To that end, the user input may correspond to a selection of a type of tissue, such as fatty or dense breast tissue, which may map to one of the transmit speeds at the host 130. Additionally or alternatively, the user input may select the second transmit speed from within a range of transmit speeds supported at the host 130. As an illustrative example, the range of transmit speeds may include transmit speeds associated with the speed of ultrasound energy within different biological materials (e.g., different tissues), such as transmit speeds between 1460 m/s and 1620 m/s.

Additionally or alternatively, the second transmit speed may be determined based on data received at the ultrasound imaging system 150. For instance, the ultrasound imaging system 150 (e.g., the host 130) may determine the second transmit speed based on an indication of the anatomical feature being imaged, a type and/or capability of a probe (e.g., probe 102) coupled to the system 150, patient data, and/or the like received and/or detected at the ultrasound imaging system 150. The indication of the anatomical feature may correspond to a user input selecting the anatomical feature. Additionally or alternatively, ultrasound imaging system 150 may identify the anatomical feature based on one or more settings, such as a depth setting, a position and/or orientation of the probe 102, and/or the like used to image the feature. In some embodiments, for instance, the ultrasound imaging system 150 may include a mapping (e.g., a table) between indications of anatomical features and the imaged anatomical feature to determine the anatomical feature. In some embodiments, the ultrasound imaging system 150 may be trained to identify the anatomical feature and/or the second transmit speed based on a deep learning network, such as a convolutional neural network (CNN), or another suitable implementation of an artificial intelligence system or structure including, for example, a random forest deep learning approach or a regression analysis approach. For instance, the ultrasound imaging system 150 may classify the data received at the ultrasound imaging system 150 as corresponding to a particular anatomical feature and/or transmit speed based on the deep learning network and/or artificial intelligence system. Further, the patient data may include a diagnosis, weight, body mass index (BMI), medical history, and/or the like associated with the patient, which may be input to the ultrasound imaging system 150 and/or retrieved from a local or remote data store (e.g., a database). The ultrasound imaging system 150 may also include a mapping (e.g., a table) between the anatomical features and/or indications of anatomical features and transmit speeds and/or between patient metrics (e.g., BMI) and transmit speeds to determine the second transmit speed.

As an illustrative example, responsive to determining that the imaged anatomical feature is relatively dense in comparison with other anatomical features, as may be the case for muscle tissue, and/or determining that the patient has a relatively low BMI (e.g., a low proportion of total fat), the second transmit speed may be determined to be relatively high. On the other hand, responsive to determining that the imaged anatomical feature is relatively dense in comparison with other anatomical features, as may be the case for muscle tissue, and/or determining that the patient has a relatively low BMI (e.g., a low proportion of total fat), the second transmit speed may be determined to be relatively high.

Moreover, in some embodiments, the second transmit speed may be determined based on analysis of ultrasound imaging data, such as data associated with the received echoes associated with the ultrasound energy transmitted at the first speed (e.g., the echoes received at step 504). For instance, in some embodiments, the ultrasound imaging system 150 may identify tissue aberration (e.g., speed of sound aberration) in an image resulting from the received echoes and/or based on the data associated with the received echoes. Based on the identified aberration, the ultrasound imaging system 150 may further determine whether to set the second transmit speed at a relatively higher or lower speed than the first transmit speed and/or a speed adjustment from the first transmit speed. For instance, the ultrasound imaging system 150 may determine a mapping of tissue aberrations in the image (e.g., over different points within the image) resulting from the received echoes and may determine the second speed of sound based on the mapping of the tissue aberrations. An example of the identification of tissue aberration within an image is described in Provisional Application No. 62/838,365, filed Apr. 25, 2019, titled "SYNTHETIC TRANSMIT FOCUSING ULTRASOUND SYSTEM WITH SPEED OF SOUND MAPPING," the entirety of which is hereby incorporated by reference.

Further, the analysis of ultrasound imaging data to determine the second transmit speed may additionally or alternatively include a comparison of ultrasound imaging data corresponding to different transmit speeds. For instance, the ultrasound imaging system 150 may control transducer array 104 to transmit ultrasound energy at a set of different transmit speeds including the first transmit speed (e.g., at step 502) and may receive echoes corresponding to the set of different transmit speeds. In some cases, the ultrasound imaging system 150 may, based on the echoes, generate a respective image for each of the set of different transmit speeds. The ultrasound imaging system 150 may then identify the image having the highest image quality and/or a particular quality, such as the highest brightness, contrast, and/or the like, from among the images. In particular, the ultrasound imaging system 150 may perform image processing, such as a pixel-level image processing (evaluating whether there is a change in the color of the pixel), to compare the images. In some embodiments, the ultrasound imaging system 150 may determine the transmit speed corresponding to the identified image as the second transmit speed.

At step 508, the method 500 involves generating multilines based on received echoes (e.g., echoes received at step 504). For instance, the host 130 may, at the multiline processors 110a-n, generate multilines based on the echoes received at the ultrasound probe 102. To that end, the multiline processors 110a-n may apply delays and/or apodization weights to the received echoes (e.g., to electrical signals corresponding to the received echoes) to form differently steered receive beams (e.g., multilines) corresponding to the same transmitted ultrasound energy.

At step 510, the method 500 involves transmit focusing multilines based on the second transmit speed. In particular, the host 130 may, using the transmit focuser 132, adjust the multilines corresponding to a particular receive line location before combining the adjusted multilines, as described below with reference to FIG. 6. Moreover, before the multilines are transmit focused, the multilines generated at step 508 may be stored at least until each multiline corresponding to the receive line location is received, as described above with reference to FIG. 2. In some embodiments, for example, the multilines may be stored in line store 112 before the host 130 adjusts the multilines based on the second transmit speed.

With reference now to FIG. 6, a flow diagram of a method 600 of transmit focusing multilines based on the second transmit speed is illustrated, in accordance with aspects of the present disclosure. In particular, the step 510 of method 500 may be implemented in accordance with one or more steps of method 600. As illustrated, the method 600 includes a number of enumerated steps, but embodiments of the method 600 may include additional steps before, after, or in between the enumerated steps. In some embodiments, one or more of the enumerated steps may be omitted, performed in a different order, or performed concurrently. The steps of the method 600 can be carried out by any suitable component within the ultrasound imaging system 150 and all steps need not be carried out by the same component. In some embodiments, one or more steps of the method 600 can be performed by, or at the direction of, a processor circuit (e.g., the processor circuit 300 (FIG. 3)) of the ultrasound imaging system 150, including the transmit focus processor 134, the image processor 122, or any other component.

At step 602, the method 600 involves determining transmit focus weights. In some embodiments, the transmit focus processor 134 may determine the transmit focus weights based on equation 1, as well as simulation of a transmit field. For instance, the transmit focus processor 134 may simulate the transmit field, and based on the simulation, the transmit focus processor 134 may determine amplitude values at different points in the simulated image field (e.g., values of the function amplitude(X, Z)). As described above with reference to equation 1 and FIG. 2, the transmit focus processor 134 may use the determined amplitude values to determine transmit focus weights for multilines corresponding to the points in the image field. In particular, the transmit focus processor 134 may determine transmit focus weights that weight the contributions of the multilines in relation to their respective proximity to a corresponding transmit beam. For instance, the transmit focus processor 134 may, based on the determined amplitude values, determine a set of transmit focus weights that increase with increasing signal-to-noise ratios at the corresponding multilines (e.g., receive line locations within the simulation).

Moreover, in some embodiments, the transmit focus processor 134 may determine the transmit focus weights based on the second transmit speed. For instance, the transmit focus processor 134 may simulate the transmit field based in part on the second transmit speed. A simulation of a transmit field may include one or more parameters corresponding to characteristics used to transmit ultrasound energy. These characteristics may include, for example, the speed of sound used to transmit the transmit beams, the size and/or shape of the transmit aperture (e.g., the number and/or arrangement of transducer elements in the transducer array 104 used to transmit the transmit beams), the focal depth of the transmit beams, and/or the like. Accordingly, to simulate the transmit field based on the second speed of sound, the transmit focus processor 134 may be configured to set one or more parameters of the simulation based on the second speed of sound. Further, based on the second transmit speed, the transmit focus processor 134 may be configured to simulate a transmit field with characteristics corresponding to or different than the values used to transmit the ultrasound energy (e.g., the first transmit speed).

For instance, if the second transmit speed is the same as the first transmit speed, the transmit focus processor 134 may simulate the transmit field with ultrasound energy transmitted at the second transmit speed. In such cases, the characteristics of the simulated transmit field may correspond to the characteristics (e.g., the first transmit speed) used to transmit the ultrasound energy using the ultrasound probe 102. As an illustrative example, if the first transmit speed and the second transmit speed is 1540 m/s, the transmit focus processor 134 may determine the transmit focus weights based on a simulation of a transmit field corresponding to the transmit speed 1540 m/s.

If, on the other hand, the second transmit speed is different from the first transmit speed, the transmit focus processor 134 may be configured to adjust the speed of sound and/or the focal depth of the simulated transmit field in comparison with the corresponding speed of sound and/or focal depth used during transmission of the ultrasound energy. As an illustrative example, if the first transmit speed is 1540 m/s and the second transmit speed is 1480 m/s, the transmit focus processor 134 may be configured to simulate the transmit field with a transmit speed of 1480 m/s. In such cases, the simulation of the transmit field may resemble the plot 450 illustrated in FIG. 4B. Additionally or alternatively, the transmit focus processor 134 may be configured to simulate the transmit field with a focal depth adjusted relative to the focal depth expected for transmission of the ultrasound energy at the first transmit speed. For instance, as illustrated by the difference between the focal depth 402 corresponding to the transmit speed 1540 m/s and the focal depth 452 corresponding to the transmit speed 1480 m/s (FIGS. 4A-B), differences in transmit speeds may result in a change in a focal depth for a transmit field. As such, adjusting the focal depth of the simulated transmit field may provide a similar effect as simulating a transmit field with the second transmit speed. In some embodiments, the transmit focus processor 134 may identify the adjusted focal depth for the simulated transmit field based on the second speed of sound. In some embodiments, for example, the transmit focus processor 134 may be configured with a mapping (e.g., a look-up table) between transmit speeds and focal depths for transmit field simulation. Thus, the transmit focus processor 134 may determine the focal depth of the transmit field simulation based on second speed of sound and the mapping, and the transmit focus processor 134 may then simulate the transmit field based on the determined focal depth for the simulation.

In any case, based on the simulation, the transmit focus processor 134 may determine the transmit focus weights. In some embodiments, the transmit focus weights may be weights applied at the transmit focuser 132 to multilines. Accordingly, the transmit focus processor 134 may configure the weights 114*a-n* based on the determined transmit focus weights.

At step 604, the method 600 involves determining transmit focus delays. In some embodiments, the transmit focus processor 134 may determine the transmit focus delays based on equation 2, as well as simulation of a transmit field. For instance, the transmit focus processor 134 may simulate the transmit field, and based on the simulation, the transmit focus processor 134 may determine propagation time (e.g., propagation delay) values at different points in the simulated image field (e.g., values of the function propagation_time(X, Z)). As described above with reference to equation 2 and FIG. 2, the transmit focus processor 134 may use the determined propagation time values to determine transmit focus delays for multilines corresponding to the points in the image field. In particular, the transmit focus processor 134 may determine transmit focus delays that equalize phase shift variance that exists from line to line for the multilines with differing transmit-receive beam location combinations. As such, signal cancellation caused by phase differences of the combined multilines may be minimized and/or avoided. For instance, the transmit focus processor 134 may determine the transmit focus delays based on the location of the multiline in relation to the center of the corresponding transmit beam within the simulated transmit field.

The transmit focus processor 134 may further determine the transmit focus delays based on the second transmit speed. For instance, as described above, the transmit focus processor 134 may simulate the transmit field based in part on the second transmit speed. Accordingly, the transmit focus processor 134 may simulate the transmit field with the second transmit speed, which may be the same as or different from the first transmit speed, and/or the transmit focus processor 134 may simulate the transmit field with a focal depth adjusted relative to the focal depth expected for transmission of the ultrasound energy at the first transmit speed. In any case, the transmit focus processor 134 may determine the transmit focus delays based on the simulation of the transmit field. Further, the transmit focus delays may be delays applied to multilines at the transmit focuser 132 (e.g., via the delay lines 118*a-n*). Accordingly, the transmit focus processor 134 configure the transmit focuser 132 and/or the delay lines 118*a-n* to apply the determined transmit focus delays.

At step 606, the method 600 involves adjusting multilines based on determined transmit focus weights and delays. As described above, the transmit focus processor 134 may configure the transmit focuser 132 to apply the determined transmit focus weights and/or delays to the multilines. To that end, adjusting the multilines based on the determined transmit focus weights may involve applying the weights 114*a-n*, which may be configured based on the transmit focus weights, to the multilines at multipliers 116*a-n*. Further, adjusting the multilines based on the determined transmit focus delays may involve delaying the multilines at delay lines 118*a-n* by the transmit focus delays.

At step 608, the method 600 involves summing the adjusted multilines. That is, for example, the multilines adjusted at step 606 may be combined. In some embodiments, the transmit focuser 132 may sum the multilines at the summer 120, which may receive the outputs of the delay lines 118*a-n* as inputs. By summing the multilines, the summer 120 may produce transmit focused image data having an extended depth of field. The summer 120 may be implemented with adder circuitry, as a digital summer, or a combination thereof.

Returning now to FIG. 5, at step 512, the method 500 may include generating an image based on the transmit focused multilines. In particular, the image processor 122 may receive the transmit focused multilines as an input and may generate the image based on the received transmit focused multilines. In some embodiments, the transmit focused multilines may correspond to image data associated with a line in the image. Accordingly, the image processor 122 may receive a set of transmit focused multilines that respectively correspond to image data associated with different lines within the image (e.g., image data received along different receive lines) and may aggregate the set of transmit focused multilines to generate the image. The image processor 122 may further perform scan conversion or other processing to improve the generated image. As described above with reference to step 510 and FIG. 6, transmit focusing the multilines may involve adjusting the multilines based on the transmit focus delays. Accordingly, the image processor 122 may generate the image based on the multilines adjusted by the transmit focus delays.

At step 514, the method 500 may involve outputting the image for display. More specifically, the image generated by the image processor 122 may be output to a display, such as display 124, which may be included in the host 130 or communicatively coupled to the host 130 (e.g., via a wired or wireless interface).

FIGS. 7A-7C illustrate transmit beam patterns resulting from retrospectively transmit focused ultrasound image data (e.g., transmit focused multilines). In FIGS. 7A-7C, the horizontal axis represents azimuth in some arbitrary units, and the vertical axis represents depth in some arbitrary units. In the embodiments illustrated in FIGS. 7A-C, each of the transmit beam patterns are determined with respect to ultrasound transmissions through a medium where the ultrasound energy propagates at a speed of 1480 m/s. To that end, the illustrated transmit beam patterns may correspond to the beam patterns resulting from retrospectively transmit focusing the transmit beam patterns illustrated in FIGS. 4A-B according to the techniques described herein (e.g., according to one or more steps of method 500 of FIG. 5 and/or method 600 of FIG. 6).

In particular, FIG. 7A illustrates a plot 700 of transmit beams corresponding to a first ultrasound transmission transmitted by the transducer array 104 at the transmit speed of 1480 m/s. The plot 700 further corresponds to ultrasound imaging data associated with the first ultrasound transmission (e.g., multilines generated based on the first ultrasound transmission) that is retrospectively transmit focused based on the transmit speed of 1480 m/s. To that end, the plot 700 illustrates transmit beam patterns corresponding to the transmit beam patterns in plot 450 of FIG. 4B after retrospective transmit focusing. That is, for example, the plot 700 may result from the adjustment, using transmit focus weights and/or delays, of the multilines and/or the received echoes associated with an ultrasound transmission transmitted with the transmit beam pattern of plot 450.

FIG. 7B illustrates a plot 720 of transmit beams corresponding to a second ultrasound transmission transmitted by the transducer array at the transmit speed of 1540 m/s. The plot 720 further corresponds to ultrasound imaging data associated with the second ultrasound transmission (e.g., multilines generated based on the second ultrasound transmission) that is transmit focused based on the transmit speed of 1540 m/s. To that end, the plot 720 illustrates transmit beam patterns corresponding to the transmit beam patterns in plot 400 of FIG. 4A after retrospective transmit focusing. Thus, the plot 720 may result from the adjustment, using transmit focus weights and/or delays, of the multilines and/or the received echoes associated with an ultrasound transmission transmitted with the transmit beam pattern of plot 400.

In comparison with the transmitted beam patterns illustrated in the plot 450, the retrospectively transmit focused beam patterns shown in plot 700 exhibit an extended depth of field (e.g., an extended focus). For instance, the retrospectively transmit focused beam patterns show in plot 700 have a narrower profile than the transmitted beam patterns illustrated in the plot 450. Similarly, in comparison with the transmitted beam patterns illustrated in the plot 400, the retrospectively transmit focused beam patterns shown in plot 720 exhibit an extended depth of field. However, in comparison with the beam patterns of plot 700, the beam patterns of plot 720 have a wider profile, which may result in lowered image resolution and/or increased blurriness in an image generated based on the beam patterns of plot 720 than an image generated based on the beam patterns of the plot 700. The discrepancies between the plot 700 and the plot 720 may result from the impact of the difference in speed between the transmit speed used at the transducer array 104 (e.g., 1540 m/s in this example) and the transmit speed that the ultrasound energy propagates at within the medium (e.g., 1480 m/s in this example) on the generation of the beam pattern of plot 720. In other words, the beam patterns of plot 720 may be distorted by tissue aberration in comparison with the beam patterns of plot 700.

FIG. 7C illustrates a plot 740 of transmit beams corresponding to a third ultrasound transmission transmitted by the transducer array at the transmit speed of 1540 m/s. The plot 740 further corresponds to ultrasound imaging data associated with the third ultrasound transmission (e.g., multilines generated based on the third ultrasound transmission) that is transmit focused based on the transmit speed of 1480 m/s. To that end, similar to the plot 720, the plot 740 illustrates transmit beam patterns corresponding to the transmit beam patterns in plot 400 of FIG. 4A after retrospective transmit focusing. However, while the plot 720 may result from transmit focusing image data corresponding to the beam patterns of plot 400 based on the transmit speed of 1540 m/s, the plot 740 may result from transmit focusing the image data corresponding to the beam patterns of the plot 400 based on the transmit speed of 1480 m/s. In further comparison with the plot 720, the beam patterns illustrated in plot 740 maintain a relatively narrower beam profile. As such, an image generated based on the beam patterns of plot 740 may appear less blurry (e.g., sharper) and have a relatively higher resolution than an image generated based on the beam patterns of the plot 720. Indeed, the beam patterns illustrated in plot 740 appear substantially similar to the beam patterns illustrated in plot 700. Thus, an image generated based on the beam patterns of plot 740 may resemble an image generated based on the beam patterns of the plot 700. In this way, plot 740 illustrates that the difference in speed between the transmit speed used at the transducer array 104 (e.g., 1540 m/s in this example) and the transmit speed that the ultrasound energy propagates at within the medium (e.g., 1480 m/s in this example) may be accounted for (e.g., the effect of the difference may be minimized) via retrospective transmit focusing, according to the techniques described herein.

FIG. 8 illustrates a plot 800 of a comparison of point spread functions (802, 804, and 806) at focal depth for different ultrasound imaging and transmit focusing techniques, as similarly described above with reference to FIGS. 7A-C. In particular, the plot 800 includes a comparison of focal quality between the techniques, where a wider spread of values over the horizontal axis represents a relatively lower focal quality and a narrower spread of values over the horizontal axis represents a relatively higher focal quality. In the illustrated embodiment, each of the point spread functions (802, 804, and 806) are determined with respect to ultrasound transmissions through a medium where the ultrasound energy propagates at a speed of 1480 m/s. In FIG. 8, the horizontal axis represents distance in some arbitrary units, and the vertical axis represents intensity in some arbitrary units.

The first point spread function 802 corresponds to a point spread function within a first image generated based on a first ultrasound transmission having a transmit speed of 1480 m/s. More specifically, the first point spread function 802 corresponds to a point spread function resulting from an image generated based on transmit focusing ultrasound data associated with the first ultrasound transmission based on the transmit speed of 1480 m/s. Accordingly, the first point spread function 802 may be associated with an image generated based on the transmit beam pattern illustrated in plot 700 of FIG. 7A.

The second point spread function 804 corresponds to a point spread function within a second image generated based on a second ultrasound transmission having a transmit speed of 1540 m/s. In particular, the second point spread function 804 corresponds to a point spread function resulting from an image generated based on transmit focusing ultrasound data associated with the second ultrasound transmission based on the transmit speed of 1540 m/s. As such, the second point spread function 804 may be associated with an image generated based on the beam pattern illustrated in plot 720 of FIG. 7B.

The third point spread function 806 corresponds to a point spread function within a third image generated based on a third ultrasound transmission having a transmit speed of 1540 m/s. In contrast with the second point spread function 804, however, the third point spread function 806 corresponds to a third image generated based on transmit focusing ultrasound data associated with the third ultrasound transmission based on the transmit speed of 1480 m/s. That is, for example, the third point spread function 806 may correspond to an image generated based on the beam patterns illustrated in plot 740 of FIG. 7C.

As shown, each of the first point spread function 802 and the third point spread function 806 are relatively similar, while the second point spread function 804 has a relatively wider profile then both the first point spread function 802 and the third point spread function 806. To that end, plot 800 further illustrates that for a given point in the corresponding images, the first and third images (e.g., corresponding to the first and third point spread functions 802 and 806, respectively) may be less blurry and more resolved than the second image (e.g., corresponding to the second point spread function 804). In other words, plot 800 further shows that the difference in speed between the transmit speed used at the transducer array 104 (e.g., 1540 m/s in this example) and the transmit speed that the ultrasound energy propagates at within the medium (e.g., 1480 m/s in this example) may be accounted for (e.g., the effect of the difference may be minimized) via retrospective transmit focusing, according to the techniques described herein.

FIGS. 9A-B illustrate ultrasound images of breast tissue that propagates ultrasound energy at a speed of approximately 1480 m/s. In FIGS. 9A-B, the horizontal axis represents azimuth in some arbitrary units, and the vertical axis represents depth in some arbitrary units. FIG. 9A illustrates an ultrasound image 900 generated based on the transmission of ultrasound energy at the transmit speed of 1540 m/s (e.g., from the transducer array 104) and transmit focusing of ultrasound data (e.g., multilines) associated with the ultrasound energy based on the transmit speed of 1540 m/s. FIG. 9B illustrates an ultrasound image 950 generated based on the transmission of ultrasound energy at the transmit speed of 1540 m/s (e.g., from the transducer array 104) and transmit focusing of ultrasound data (e.g., multilines) associated with the ultrasound energy based on the transmit speed of 1480 m/s. As illustrated, the image quality of the ultrasound image 950 is better in terms of resolution and/or sharpness than the ultrasound image 900. Accordingly, FIGS. 9A-B further demonstrate the benefits of the techniques described herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
an array of acoustic elements configured to transmit ultrasound energy at a first transmit speed and receive echoes associated with the ultrasound energy transmitted at the first transmit speed; and
a processor circuit in communication with the array of acoustic elements and configured to:
generate a plurality of multilines based on the received echoes;
determine a second transmit speed;
determine a set of transmit focus delays based on the second transmit speed;
adjust the plurality of multilines using the set of transmit focus delays;
generate an image based on the adjusted plurality of multilines; and
output the generated image to a display in communication with the processor circuit.

2. The ultrasound imaging system of claim 1, further comprising a plurality of delay lines in communication with the array of acoustic elements and the processor circuit, wherein the processor circuit is further configured to control the plurality of delay lines to delay the plurality of multilines according to the set of transmit focus delays to adjust the plurality of multilines.

3. The ultrasound imaging system of claim 1, wherein the processor circuit is further configured to:
determine a set of transmit focus weights based on the second transmit speed; and
adjust the plurality of multilines using the set of transmit focus weights.

4. The ultrasound imaging system of claim 3, further comprising a multiplier in communication with the array of acoustic elements and the processor circuit, wherein the processor circuit is further configured to control the multiplier to apply the set of transmit focus weights to the plurality of multilines to adjust the plurality of multilines.

5. The ultrasound imaging system of claim 1, further comprising a summer in communication with the processor circuit and the array of acoustic elements, wherein the summer is configured to sum the adjusted plurality of multilines to produce transmit focused image data, and wherein the processor circuit is configured to generate the image further based on the transmit focused image data.

6. The ultrasound imaging system of claim 1, wherein the processor circuit is configured to determine the set of transmit focus delays further based on a model of ultrasound energy transmitted at the second transmit speed.

7. The ultrasound imaging system of claim 1, wherein the array of acoustic elements is configured to transmit the ultrasound energy with a first focal depth, and wherein the processor circuit is configured to determine the set of transmit focus delays further based on a model of ultrasound energy transmitted with a second focal depth.

8. The ultrasound imaging system of claim 7, wherein the processor circuit is further configured to determine the second focal depth based on the second transmit speed.

9. The ultrasound imaging system of claim 1, wherein the ultrasound energy comprises a plurality of ultrasound beams, and wherein the array of acoustic elements is configured to transmit each of the plurality of ultrasound beams from a respective transmit beam location.

10. The ultrasound imaging system of claim 9, wherein the plurality of multilines correspond to imaging data associated with a receive line location along which the echoes are received for each of the plurality of ultrasound beams.

11. The ultrasound imaging system of claim 1, wherein the processor circuit is configured to determine the second transmit speed based on a user input.

12. The ultrasound imaging system of claim 11, wherein the user input comprises a selection of the second transmit speed from among a set of predetermined transmit speeds.

13. The ultrasound imaging system of claim 1, wherein the processor circuit is configured to generate the image further based on an additional adjusted plurality of multilines, wherein the adjusted plurality of multilines corresponds to a first line of the image, and the additional adjusted plurality of multilines corresponds to a second line of the image.

14. The ultrasound imaging system of claim 1, further comprising the display.

15. A method of retrospectively transmit focusing ultrasound data for ultrasound imaging, comprising:

controlling, by a processor circuit, an array of acoustic elements in communication with the processor circuit to transmit ultrasound energy at a first transmit speed and receive echoes associated with the transmitted ultrasound energy;

generating, by the processor circuit, a plurality of multilines based on the received echoes;

determining, by the processor circuit, a second transmit speed;

determining, by the processor circuit, a set of transmit focus delays based on the second transmit speed;

adjusting, by the processor circuit, the plurality of multilines using the set of transmit focus delays;

generating, by the processor circuit, an image based on the adjusted plurality of multilines; and outputting, by the processor circuit, the generated image to a display in communication with the processor circuit.

* * * * *